United States Patent
Cortez et al.

(10) Patent No.: US 9,469,652 B2
(45) Date of Patent: Oct. 18, 2016

(54) ERK INHIBITORS

(71) Applicant: Eli Lilly and Company, Indianapolis, IN (US)

(72) Inventors: Guillermo S. Cortez, Indianapolis, IN (US); Sajan Joseph, Carmel, IN (US); Johnathan Alexander McLean, Indianapolis, IN (US); William T. McMillen, McCordsville, IN (US); Michael John Rodriguez, Indianapolis, IN (US); Gaiying Zhao, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/970,588

(22) Filed: Dec. 16, 2015

(65) Prior Publication Data

US 2016/0176896 A1  Jun. 23, 2016

Related U.S. Application Data

(60) Provisional application No. 62/095,185, filed on Dec. 22, 2014.

(51) Int. Cl.
*C07D 495/04* (2006.01)
*C07D 498/08* (2006.01)

(52) U.S. Cl.
CPC ............ *C07D 495/04* (2013.01); *C07D 498/08* (2013.01)

(58) Field of Classification Search
None
See application file for complete search history.

(56) References Cited

U.S. PATENT DOCUMENTS

2003/0064982 A1   4/2003   Davies et al.

FOREIGN PATENT DOCUMENTS

| WO | 2007/053776 A1 | 5/2007 |
| WO | 2010/022121 A1 | 2/2010 |
| WO | 2013/130976 A1 | 9/2013 |
| WO | 2013130976 | * 9/2013 |

OTHER PUBLICATIONS

Document from WIPO Examination of related application: "Written Opinion of the International Search Authority," Date of completion of this opinion as per Form PCT/ISA/237: Date of the actual completion of the International search: Mar. 23, 2016, Date of mailing of the International search report: Apr. 5, 2016.

Document from WIPO Examination of related application: "International Search Report," Form PCT/ISA/220, Date of the actual completion of the International search: Mar. 23, 2016, Date of mailing of the International search report: Apr. 5, 2016.

* cited by examiner

*Primary Examiner* — Karl J Puttlitz
(74) *Attorney, Agent, or Firm* — Danica Hostettler

(57) ABSTRACT

The present invention provides thieno[2,3-c]pyrrol-4-one compounds that inhibit activity of extracellular-signal-regulated kinase (ERK) and may be useful in the treatment of cancer.

42 Claims, No Drawings

ERK INHIBITORS

The present invention relates to thieno[2,3-c]pyrrol-4-one compounds, or pharmaceutically acceptable salts thereof, and pharmaceutical compositions comprising the compounds, that inhibit activity of extracellular-signal-regulated kinase (ERK) and may be useful for treating cancer.

The ERK/MAPK pathway is important for cell proliferation and frequently observed to be activated in many tumors. RAS genes, which are upstream of ERK1/2, are mutated in several cancers including colorectal, melanoma, non-small cell lung cancer as well as breast and pancreatic tumors. High RAS activity is accompanied by elevated ERK activity in many human tumors. Studies have also shown that ERK is a critical component of RAS signalling. These observations support the attractiveness of the ERK1/2 signaling pathway for developing anticancer therapies in a broad spectrum of human tumors.

ERK inhibitors are known in the art; see, for example, WO2013130976. Additionally, other aminopyrimidine compounds are known in the art; see, for example, WO 2010/022121. There remains a need to provide alternative ERK inhibitors, more particularly for the treatment of cancer. Accordingly, the present invention provides ERK1/2 inhibitors which may be useful for treating cancer.

The present invention provides a compound of the following formula:

Formula I

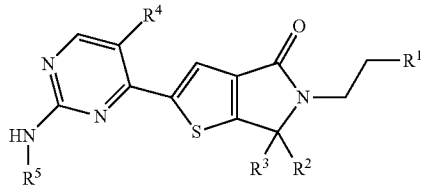

wherein:
$R^1$ is

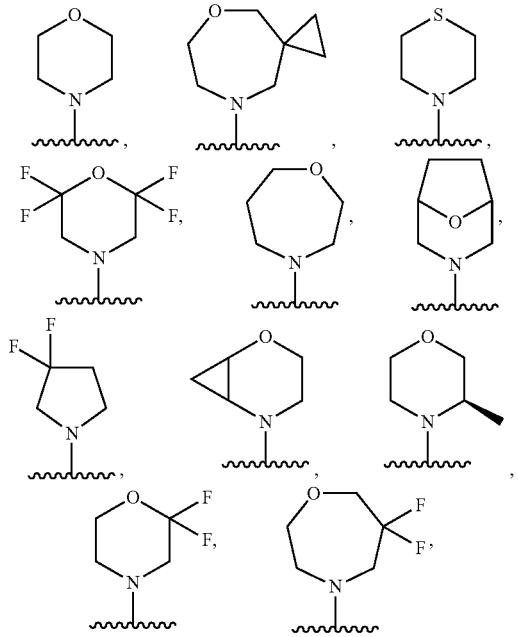

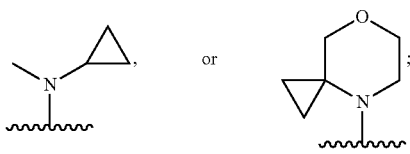

$R^2$ and $R^3$ are independently methyl or $R^2$ and $R^3$ can be taken together to form cyclopropyl;

$R^4$ is hydrogen, methyl, chloro, fluoro, or trifluromethyl; and $R^5$ is

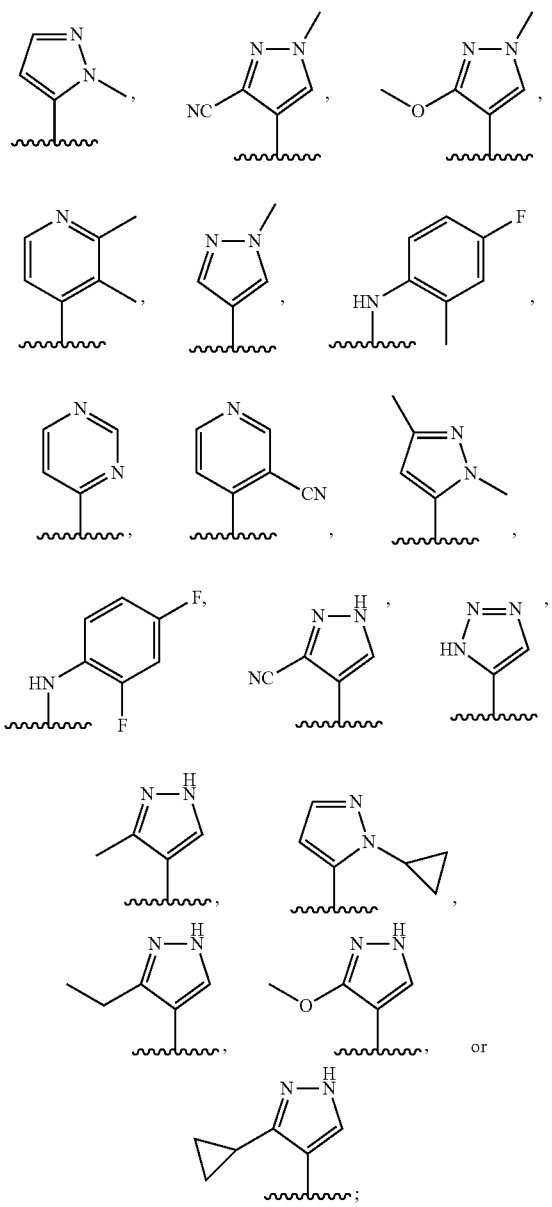

or a pharmaceutically acceptable salt thereof.

The present invention also provides a compound of the following formula:

Formula I

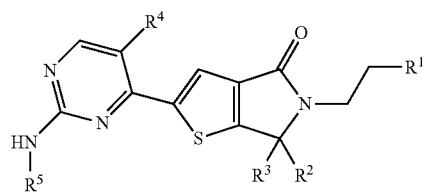

wherein:
R¹ is

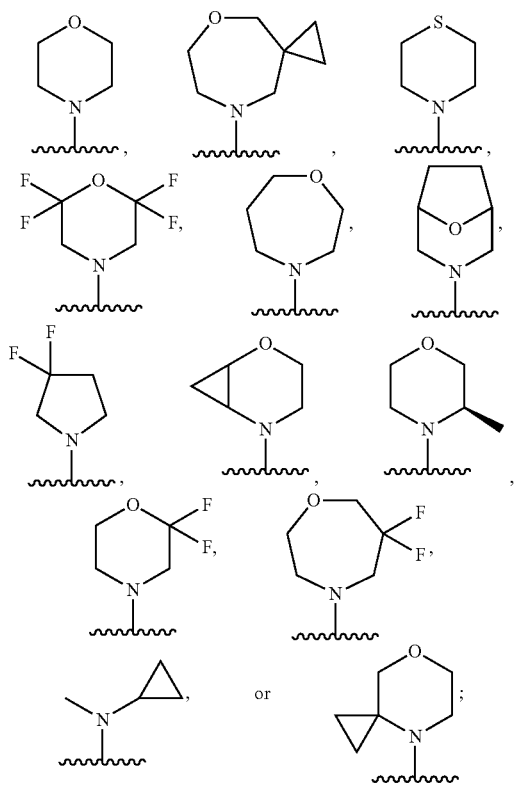

R² and R³ are independently methyl or R² and R³ can be taken together to form cyclopropyl;
R⁴ is hydrogen, methyl, chloro, fluoro, or trifluoromethyl; and
R⁵ is

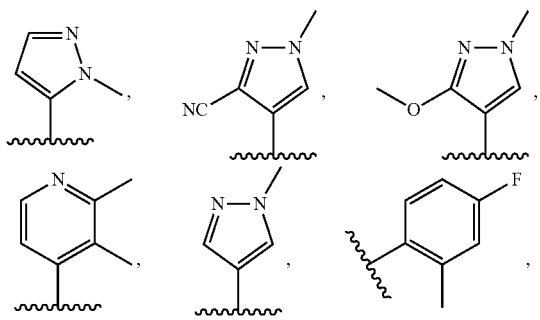

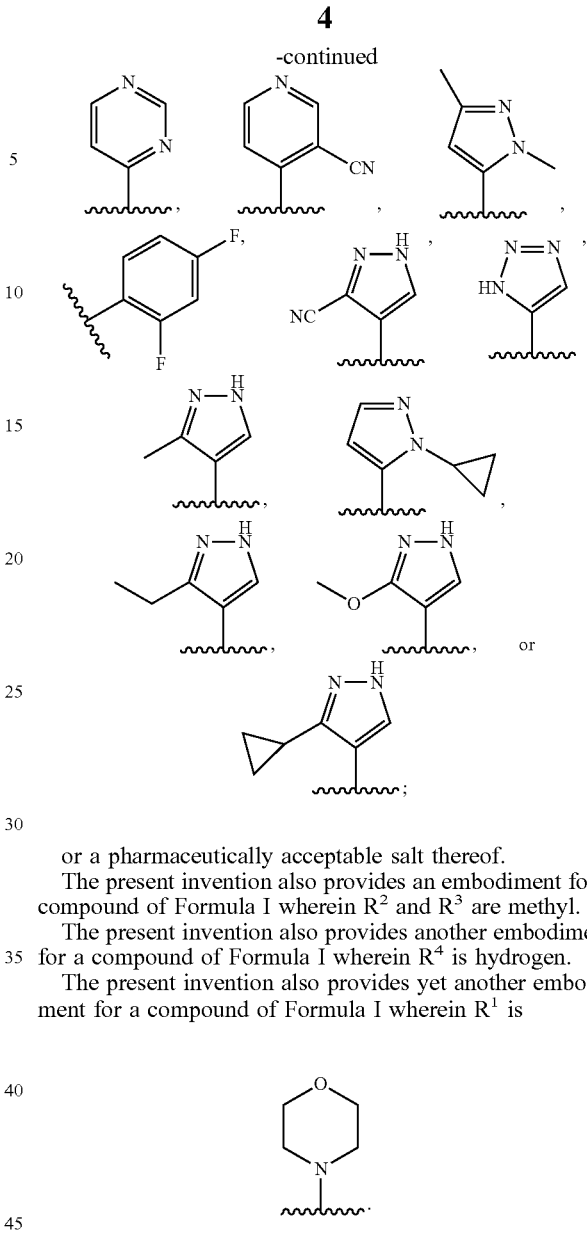

or a pharmaceutically acceptable salt thereof.

The present invention also provides an embodiment for a compound of Formula I wherein R² and R³ are methyl.

The present invention also provides another embodiment for a compound of Formula I wherein R⁴ is hydrogen.

The present invention also provides yet another embodiment for a compound of Formula I wherein R¹ is

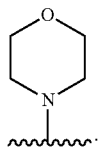

The present invention also provides yet a further embodiment for a compound of Formula I wherein R⁵ is

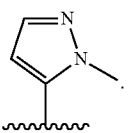 [SMILES: *c1ccnn1C]

Preferably, the present invention provides a compound which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof.

As a particular embodiment, the present invention provides the compound which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

The present invention provides a pharmaceutical composition comprising 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof, and a pharmaceutically acceptable carrier, diluent, or excipient. The present invention provides a pharmaceutical composition comprising 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, and a pharmaceutically acceptable carrier, diluent, or excipient.

The present invention provides a method for treating cancer comprising administering to a patient in need thereof an effective amount of 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof. The present invention provides a method for treating cancer comprising administering to a patient in need thereof an effective amount 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

The present invention provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof, for use in therapy. The present invention provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof, for use in the treatment of cancer. The present invention provides a pharmaceutical composition for use in treating cancer, the pharmaceutical composition comprising 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof.

The present invention also provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one for use in therapy. The present invention provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one for use in the treatment of cancer. The present invention provides a pharmaceutical composition for use in treating cancer, the pharmaceutical composition comprising 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

The present invention provides the use of 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof, in the manufacture of a medicament for the treatment of cancer. The present invention also provides the use of 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one in the manufacture of a medicament for the treatment of cancer.

The present invention provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one in a crystalline form. The present invention also provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one in a crystalline form characterized by a X-ray powder diffraction pattern having characteristic peaks, in 2θ±0.2°, occurring at 19.3° in combination with one or more of the peaks selected from the group consisting of 15.5°, 17.1°, 18.0°, 20.2°, 21.5° and 22.1°.

Furthermore, the present invention provides preferred embodiments of the methods and uses as described herein, in which cancer is selected from the group consisting of melanoma, colorectal cancer, pancreatic cancer, and non-small cell lung cancer. Preferred cancers are colorectal cancer, pancreatic cancer, and non-small cell lung cancer.

The present invention also provides 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one, or a pharmaceutically acceptable salt thereof, for use in simultaneous, separate or sequential administration in combination with one or more chemotherapy agents in the treatment of cancer. Preferred chemotherapy agents for such a combination are a pan-RAF inhibitor compound, more particularly 1-(3,3-dimethylbutyl)-3-(2-fluoro-4-methyl-5-(7-methyl-2-(methylamino)pyrido[2,3-d]pyrimidin-6-yl)phenyl)urea, a CDK4/6 inhibitor compound, more particularly palbociclib, ribociclib, or [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, or an anti-VEGFR2 antibody, more particularly ramucirumab. Additional preferred chemotherapy agents for such a combination are a TGF-beta receptor kinase inhibitor compound, more particularly galunisertib (see WO 2004/048382), an ALK-5 kinase inhibitor, more particularly EW-7197, a MEK inhibitor compound, more particularly cobimetinib or trametinib, or a Notch inhibitor compound, more particularly 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide (see WO 2013/016081). Further additional preferred chemotherapy agents for such a combination are a PD-L1 (Programmed death-ligand 1) inhibitor or a PD-1 (Programmed death 1) inhibitor.

The present invention preferably contains compounds of Formula I with the following substituents:

a) R1 is

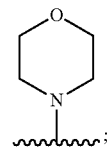

b) R2 is methyl;

c) R3 is methyl;

d) R4 is hydrogen; or e) R5 is

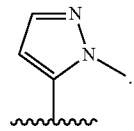

More preferably, the present invention contains compounds of Formula I with the following combinations of substituents:

a) $R^2$ and $R^3$ are methyl;
b) $R^2$ is methyl, $R^3$ is methyl, and $R^4$ is hydrogen;
c) $R^1$ is

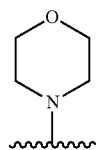

and $R^5$ is

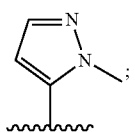

d) $R^2$ is methyl, $R^3$ is methyl, $R^4$ is hydrogen, and $R^1$ is

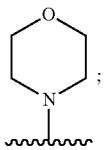 [SMILES: *N1CCOCC1]

e) $R^2$ is methyl, $R^3$ is methyl, $R^4$ is hydrogen, and $R^5$ is

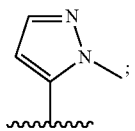

or
f) $R^2$ is methyl, $R^3$ is methyl, $R^4$ is hydrogen, and $R^1$ is

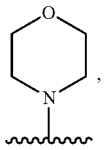

and $R^5$ is

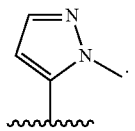

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans "Pharmaceutically acceptable salts" or "a pharmaceutically acceptable salt" refers to the relatively non-toxic, inorganic and organic salt or salts of the compound of the present invention.

"Effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

It will be understood by the skilled artisan that compounds of the present invention are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

The compounds of the present invention are preferably formulated as pharmaceutical compositions administered by a variety of routes. Preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al., 21$^{st}$ ed., Mack Publishing Co., 2005).

The compounds of the present invention are generally effective over a wide dosage range. For example, dosages per day normally fall within the daily range of about 1 to 2000 mg. Preferably such doses fall within the daily range of 50 to 1000 mg. More preferably such doses fall within the daily range of 125 to 400 mg. In some instances dosage levels below the lower limit of the aforesaid ranges may be more than adequate, while in other cases still larger doses may be employed, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The skilled artisan will appreciate that certain compounds of the present invention contain at least one chiral center. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

The designation of "isomer 1" in a compound name represents that the corresponding intermediate or compound of the present invention is the first of two eluting enantiomers when a mixture of a pair of enantiomers is separated by chiral chromatography. The designation of "isomer 2" in a compound name represents that the corresponding intermediate or compound of the present invention that is the second of two eluting enantiomers when the mixture of a pair of enantiomers is separated by chiral chromatography.

The compounds of the present invention can be prepared according to synthetic methods well known and appreciated in the art. Suitable reaction conditions for the steps of these reactions are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

As used herein, the following terms have the meanings indicated: "ACN" refers to acetonitrile; "DCM" refers to dichloromethane; "DMF" represents N,N-dimethylformamide; "DMSO" refers to dimethyl sulfoxide; "DTT" refers to dithiothreitol; "EDTA" refers to ethylenediaminetetraacetic acid; "EGTA" refers to ethylene glycol tetraacetic acid; "ELISA" refers to enzyme-linked immunosorbent assay; "EtOAc" refers to ethyl acetate; "EtOH" refers to ethanol; "FBS" refers to fetal bovine serum; "HBSS" refers to Hank's Balanced Salt Solution; "IC$_{50}$" refers to half maximal inhibitory concentration; "IVTI" refers to in vivo target inhibition; "MS" refers to mass spectroscopy; "MeOH" refers to methanol; "NMR" refers to nuclear magnetic resonance; "PBST" refers to phosphate buffered saline containing Tween-20; "THF" refers to tetrahydrofuran; "UVW" refers to ultra-violet wavelength, and "XRD" refers to X-ray diffraction.

Unless noted to the contrary, the compounds illustrated herein are named and numbered using either ACDLABS or Accelrys Draw 4.1.

Compounds of the present invention may be synthesized as illustrated in the following schemes, where $R^1$, $R^2$, $R^3$, $R^4$, and $R^5$ are as previously defined.

Scheme 1: Synthesis of Compounds of Formula I

Scheme 1 illustrates the general synthesis of compounds of Formula I. Compound 1 is reacted with a suitably substituted Compound 2 under well-known aromatic substitution or coupling reaction conditions to provide a compound of Formula I. More specifically, Compound 1 is reacted with Compound 2 at elevated temperature in the presence of a suitable base such as sodium hydride, isopropylmagnesium chloride, cesium carbonate, potassium carbonate or tert-butoxide. Optionally, introduction of a suitable ligand agent such as 4,5-bis(diphenylphosphino)-9,9-dimethylxanthene or 2-(di-tert-butylphosphino)-2',4',6'-triisopropyl-3,6-dimethoxy-1,1'-biphenyl, and a suitable catalyst such as palladium(II)acetate, tris(dibenzylideneacetone)dipalladium(0) or chloro[2-(di-tert-butylphosphino)-2',4',6'-triisopropyl-1,1'-biphenyl][2-(2-aminoethyl)phenyl)]palladium(II) in an appropriate solvent such as 1,4-dioxane or tert-butyl alcohol may also provide a compound of Formula I.

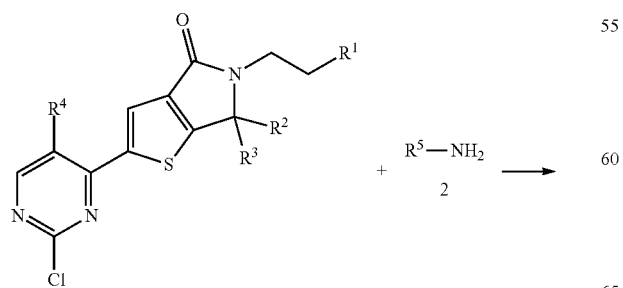

PG is nitrogen protecting group

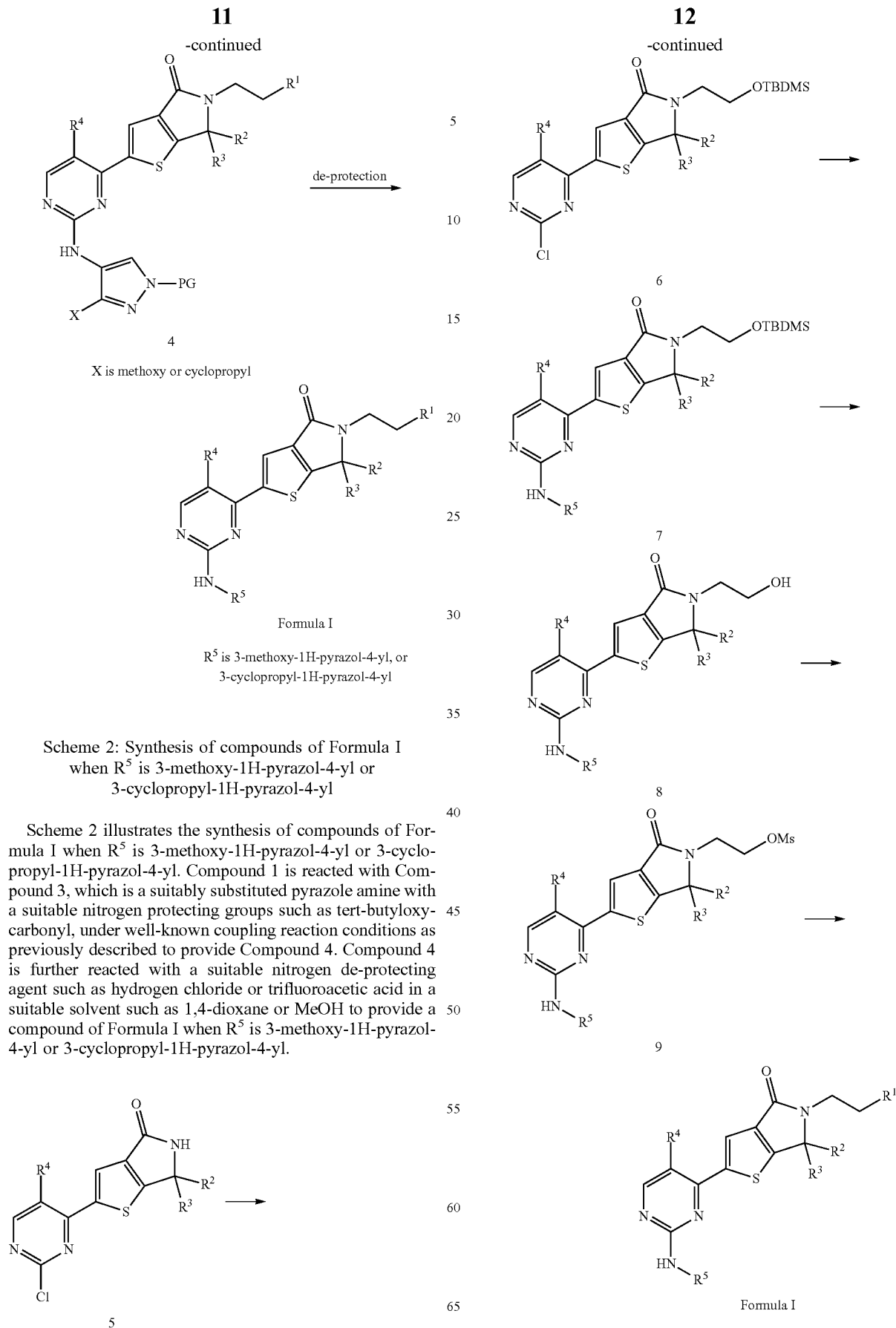

Scheme 2: Synthesis of compounds of Formula I when $R^5$ is 3-methoxy-1H-pyrazol-4-yl or 3-cyclopropyl-1H-pyrazol-4-yl Scheme 2 illustrates the synthesis of compounds of Formula I when $R^5$ is 3-methoxy-1H-pyrazol-4-yl or 3-cyclopropyl-1H-pyrazol-4-yl. Compound 1 is reacted with Compound 3, which is a suitably substituted pyrazole amine with a suitable nitrogen protecting groups such as tert-butyloxycarbonyl, under well-known coupling reaction conditions as previously described to provide Compound 4. Compound 4 is further reacted with a suitable nitrogen de-protecting agent such as hydrogen chloride or trifluoroacetic acid in a suitable solvent such as 1,4-dioxane or MeOH to provide a compound of Formula I when $R^5$ is 3-methoxy-1H-pyrazol-4-yl or 3-cyclopropyl-1H-pyrazol-4-yl.

Scheme 3: Alternative Synthesis of Compounds of Formula I

Scheme 3 illustrates an alternative synthesis of compounds of Formula I. Compound 5 is reacted with (2-bromoethoxy)-tert-butyldimethylsilane in the presence of a suitable base such as sodium hydride in a suitable solvent such as DMF to provide Compound 6. Compound 6 is then reacted with a suitably substituted Compound 2 ($R^5$—$NH_2$) under well-known coupling reaction conditions as previously described to provide Compound 7. Compound 7 is reacted with a suitable de-protecting agent such as acetic acid in a suitable solvent such as a mixture of THF and water to provide Compound 8. Compound 8 is further reacted with methanesulfonyl chloride in a suitable solvent such as DMF in the presence of a suitable base such as triethylamine to provide Compound 9. Compound 9 is reacted with a suitable amine in a suitable solvent such as ACN to provide a compound of Formula I.

Scheme 4: Synthesis of Compound 1

Scheme 4 illustrates the method for the synthesis of Compound 1. Compound 10 is reacted with a suitable bromination agent such as N-bromosuccinimide in a suitable solvent such as ACN to provide Compound 11. Compound 11 is reacted with a suitable base such as sodium hydride or sodium hydroxide, and a suitable N-alkylation agent such as 4-(2-chloroethyl)morpholine to provide Compound 12. Compound 12 is reacted with bis(pinacolato)diboron, a suitable base such as potassium acetate, and a suitable catalyst such as (1,1'-bis(diphenylphosphino)ferrocene)palladium(II) chloride in a suitable solvent such as 1,4-dioxane under an elevated temperature to provide Compound 13. Compound 13 is reacted with a suitably substituted pyrimidine compound such as 2,4-dichloro-5-methylpyrimidine, a suitable base such as potassium carbonate, a suitable catalyst such as tetrakis(triphenylphosphine)palladium in a suitable solvent such as a mixture of 1,4-dioxane and water under an elevated temperature to provide Compound 1.

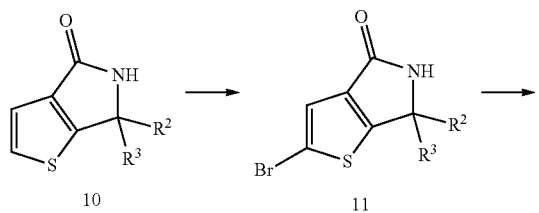

10    11

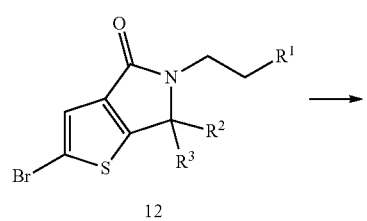

12

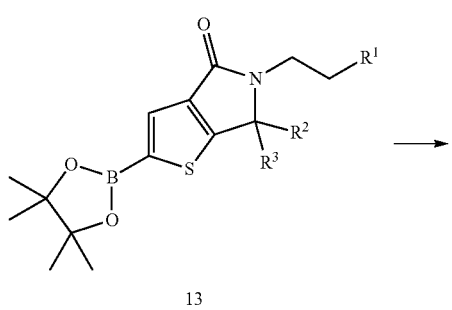

13

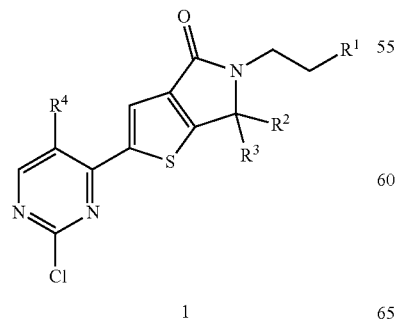

1

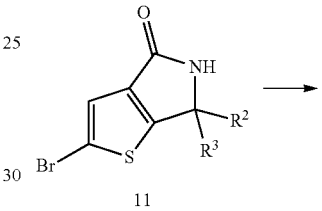

11

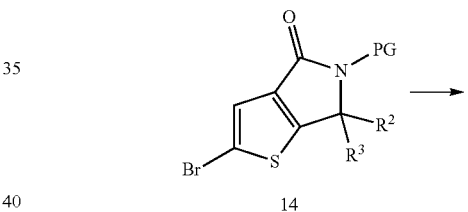

14

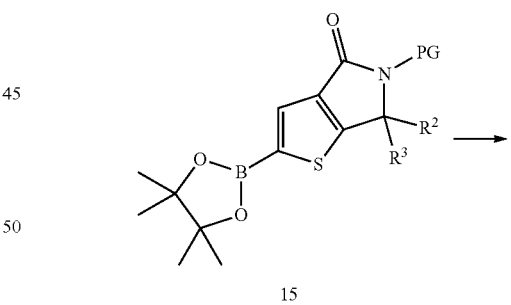

15

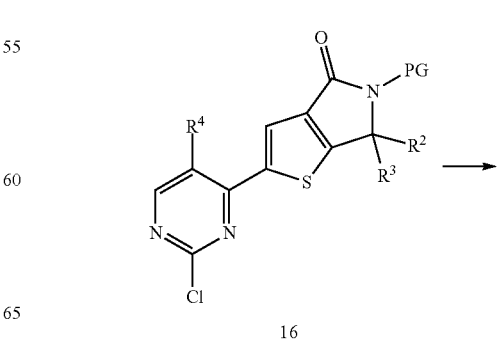

16

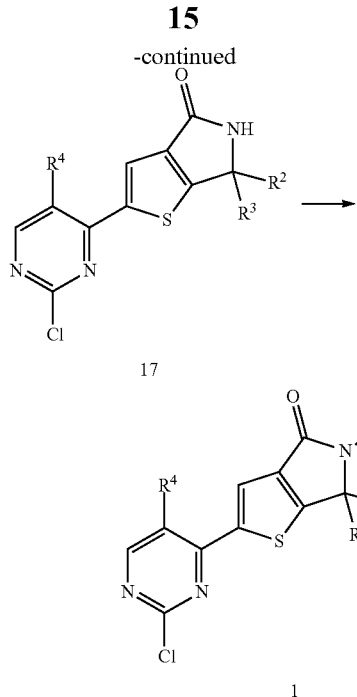

Scheme 5: Alternative Synthesis of Compound 1

Scheme 5 illustrates an alternative method for the synthesis of Compound 1. Compound 11 is reacted with a suitable nitrogen protecting agent such di-tert-butyldicarbonate in a suitable solvent such as ACN in the presence of a suitable base such as N,N-diisopropylethylamine to provide Compound 14. Compound 14 is reacted with bis(pinacolato)diboron under well-known coupling reaction conditions as previously described to provide Compound 15. Compound 15 is reacted with a suitably substituted pyrimidine compound under well-known coupling reaction conditions as previously described to provide Compound 16. Compound 16 is de-protected with a suitable de-protecting agent such as trifluoroacetic acid or hydrogen chloride in a suitable solvent such as DCM or 1,4-dioxane to provide Compound 17. Compound 17 is reacted with a suitable alkylation agent such as 4-(2-bromoethyl)morpholine in a suitable solvent such as N-methylpyrrolidone in the presence of a suitable base such as sodium hydride to provide Compound 1.

Preparation 1

6,6-Dimethylthieno[2,3-c]furan-4-one

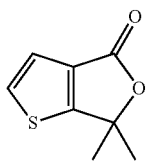

Cool a solution of 3-thiophenecarboxylic acid (250 g, 1.95 mol) in THF (9750 mL) to −70° C. in a 20 L 3-neck flask. To this solution, add n-butyl lithium (2.5 M in hexane, 1872 mL, 4.68 mol) slowly while maintaining the temperature below −55° C. Stir the reaction mixture for one hour at −70° C. Add acetone (187 mL, 2.55 mol) slowly at −70° C. Allow the reaction mixture to warm to 0° C. and stir for three hours at 0° C. To the resulting solution, add 4 M HCl (1500 mL) at 0° C. and allow the reaction mixture to warm to room temperature. Stir the resulting mixture overnight. Filter the reaction mixture through a diatomaceous earth pad and wash the pad with toluene (3×500 mL). Concentrate the filtrate under reduced pressure. Dissolve the resulting crude residue in toluene (3750 mL) and water (250 mL) and add p-toluene sulfonic acid (100.1 g, 0.526 mol) at room temperature. Reflux the reaction mixture for 16 hours at 100° C. Cool the reaction to room temperature and concentrate under reduced pressure at 50° C. Dissolve the resulting residue in water and extract with EtOAc (2×10 L). Wash the organic layer with saturated aqueous sodium bicarbonate and water. Dry the organic layer over anhydrous sodium sulfate, filter and concentrate the filtrate under reduced pressure at 50° C. to provide the title compound 200 g (61%) as brown viscous liquid. MS (m/z): 169 (M+1).

Preparation 2

6,6-Dimethyl-5H-thieno[2,3-c]pyrrol-4-one

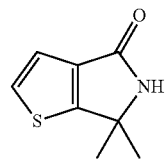

Charge a 5 L autoclave with a solution of 6,6-dimethyl-thieno[2,3-c]furan-4-one (150 g, 0.891 mol) in ammonium hydroxide (1000 ml). In a closed environment, bring the reaction mixture carefully to a temperature of 200° C. and stir for four hours at 200° C. After four hours, cool the reaction mixture to room temperature and release the ammonia gas. Extract the reaction mixture with DCM (3×750 mL). Wash the organic layer with water (1×750 mL), and dry over anhydrous sodium sulfate, filter and concentrate the filtrate under reduced pressure at 50° C. to give the title compound 100 g (67%). MS (m/z): 168 (M+1).

Preparation 3

Methyl 2-bromothiophene-3-carboxylate

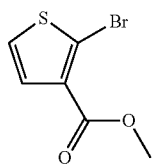

Treat a solution of 2-bromo-3-thiophenecarboxylic acid (10.1 g, 49 mmol) in MeOH (100 mL) with sulfuric acid (2.5 mL, 45 mmol). Heat the reaction to reflux overnight. Concentrate the mixture under reduced pressure to remove the organic solvent and pour the resulting mixture into ice cold water. Extract the cold solution with EtOAc. Wash the combined organic extracts with water followed by a saturated aqueous sodium bicarbonate solution. Dry the organic solution over anhydrous sodium sulfate, filter and concentrate the filtrate under reduced pressure to give the title compound 10.77 g (100%). ¹H NMR (400.15 MHz, DMSO-d₆) δ 7.65 (d, J=6 Hz, 1H), 7.34 (d, J=6 Hz, 1H), 3.78 (s, 3H).

Preparation 4

Methyl 2-cyanothiophene-3-carboxylate

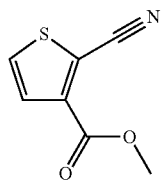

Heat a mixture of methyl 2-bromothiophene-3-carboxylate (28 g, 128 mmol) and copper cyanide (15 g, 167 mmol) in N-methylpyrrolidone (130 mL) to 120° C. overnight. Cool the reaction to room temperature and dilute with EtOAc. Wash the organic solution with saturated NaCl, dry over anhydrous sodium sulfate, filter and concentrate the filtrate under reduced pressure. Purify the residue by silica gel column chromatography eluting with 25% EtOAc in hexane to give the title compound 15.2 g (71%). ¹H NMR (400.15 MHz, DMSO-d₆) δ 8.10 (d, J=5 Hz, 1H), 7.58 (d, J=5 Hz, 1H), 3.86 (s, 3H).

Preparation 5

Spiro[5H-thieno[2,3-c]pyrrole-6,1'-cyclopropane]-4-one

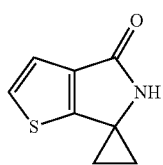

Treat a −70° C. solution of methyl 2-cyanothiophene-3-carboxylate (13.7 g, 79 mmol) and titanium tetra(isopropoxide) (24.8 g, 87.4 mmol) in diethyl ether (330 mL) with a solution of ethylmagnesium bromide (3 M in diethyl ether, 58 mL, 175 mmol). Stir the reaction mixture for 60 minutes. Remove the cooling bath and allow the mixture to slowly warm to room temperature over one hour. Add boron trifluoride etherate (22.6 mL, 159 mmol) and stir the mixture for an additional one hour. Quench the reaction with 1 N hydrochloric acid (240 mL) and stir overnight. Separate the organic layer and back extract the aqueous layer with additional ether. Combine the organic extracts and wash with saturated aqueous sodium bicarbonate and saturated NaCl. Dry the organic solution over anhydrous sodium sulfate, filter and concentrate the filtrate under reduced pressure. Purify the residue by HPLC on a C18 column (Column: 275 g; Mobile Phase: A) 0.10% formic acid in water, B) 0.10% formic acid in ACN; Gradient: 5-35% B; Flow Rate: 80 mL/min) to give the title compound 1.02 g (35%). ¹H NMR (400.15 MHz, DMSO-d₆) δ 8.43 (bs, 1H), 7.53 (d, J=5 Hz, 1H), 7.12 (d, J=5 Hz, 1H), 1.51 (m, 2H), 1.38 (m, 2H).

Preparation 6

2-Bromo-6,6-dimethyl-5H-thieno[2,3-c]pyrrol-4-one

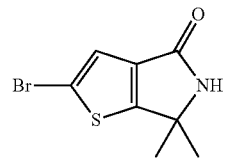

To a 20 L flask containing 6,6-dimethyl-5H-thieno[2,3-c]pyrrol-4-one (835 g, 4.99 mol) add ACN (10000 mL) and cool the solution to 10° C. Add N-bromosuccinimide (444.4 g, 2.49 mol) in four equal portions to the reaction mixture and stir for six hours at 25° C. Concentrate the reaction mixture under reduced pressure and slurry the resulting compound in water and extract with EtOAc (3×4.1 L). Wash the combined organic extracts with water (3×4.1 L) and saturated NaCl (4.1 L), dry over anhydrous sodium sulfate and filter. Store the organic solution for combination with additional batches.

Using the same process as above, prepare two additional batches starting with 650 g and 835 g 6,6-dimethyl-5H-thieno[2,3-c]pyrrol-4-one respectively. Combine the organic solutions from all three runs and concentrate under reduced pressure at 50° C. to yield 2-bromo-6,6-dimethyl-5H-thieno[2,3-c]pyrrol-4-one as brown sticky material. Slurry the resulting product in diethyl ether/hexane (2:1 v/v) and filter to yield the title compound 1542 g (45%). MS (m/z): 246/248 (M+1/M+3).

The following compound is prepared essentially by the method of Preparation 6.

| Prep. No. | Compound Name | Structure | MS (m/z): |
|---|---|---|---|
| 7 | 2-Bromospiro[5H-thieno[2,3-c]pyrrole-6,1'-cyclopropane]-4-one | 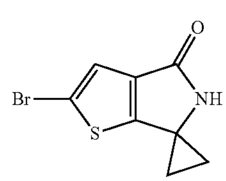 | 244/246 (M + 1/M + 3) |

Preparation 8

4-(2-Bromoethyl)morpholine hydrobromide

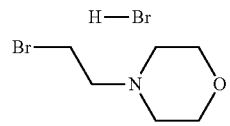

Treat a solution of triphenylphosphine dibromide (124 g, 293 mmol) in DCM (2.44 L) with a solution of 4-morpholineethanol (32 g, 244 mmol) in DCM (60 mL) dropwise over one hour while maintaining the reaction temperature below 25° C. Stir the mixture overnight at room temperature. Conduct an additional reaction as above starting with 4-morpholineethanol (10 g, 76 mmol), scaling the reagents appropriately. Combine the reaction mixtures and collect the solids by vacuum filtration to give the title compound 76.7 g (84%). $^1$H NMR (399.8 MHz, DMSO-$d_6$) δ 4.05 (m, 2H), 3.84 (m, 2H), 3.78 (t, J=7 Hz, 1H), 3.67 (t, J=7 Hz, 2H), 3.56 (m, 2H), 3.26 (m, 2H).

Preparation 9 tert-Butyl 2-bromo-6,6-dimethyl-4-oxo-thieno[2,3-c]pyrrole-5-carboxylate

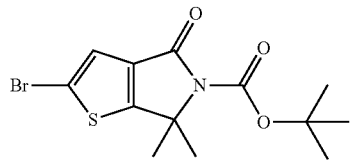 [SMILES: CC(C)(C)OC(=O)N1C(=O)c2cc(Br)sc2C1(C)C]

Synthetic Method 1:

Treat a solution of 2-bromo-6,6-dimethyl-5H-thieno[2,3-c]pyrrol-4-one (25 g, 102 mmol), 4-dimethylaminopyridine (1.25 g, 10 mmol) and N,N-diisopropylethylamine (24 mL, 138 mmol) in ACN (481 mL) with di-tert-butyldicarbonate (35 g, 162 mmol). Stir the mixture overnight at room temperature. Concentrate the mixture under reduced pressure. Dilute the mixture with hexane, filter the mixture through a silica gel pad and elute the pad with hexane followed by 20% DCM in hexane. Concentrate the filtrate to dryness to give the title compound 36.5 g (93%) as an orange oil. $^1$H NMR (399.8 MHz, CDCl$_3$) δ 7.19 (s, 1H), 1.74 (s, 6H), 1.58 (s, 9H).

Synthetic Method 2:

Treat a solution of 2-bromo-6,6-dimethyl-5H-thieno[2,3-c]pyrrol-4-one (200 g, 813 mmol), N,N-dimethylpyridin-4-amine (9.93 g, 81 mmol) and di-tert-butyldicarbonate (266 g, 1219 mmol) in ACN (2 L) dropwise with N,N-diisopropylethylamine (213 mL, 1219 mmol). Stir the mixture at room temperature for four hours. Heat the reaction to 30° C. for two hours. Cool the mixture to room temperature and stir overnight. Concentrate the mixture under reduced pressure. Dilute the mixture with EtOAc and wash the resulting organic solution twice with water (300 mL) followed by saturated NaCl (300 mL). Dry the organic solution over anhydrous sodium sulfate, filter and concentrate the filtrate under reduced pressure. Purify the residue on a silica gel pad eluting with a gradient from 0-20% EtOAc in hexane to give the title compound 253 g (90%). MS (m/z): 290/292 (M-isobutene+1/M-isobutene+3). $^1$H NMR (399.8 MHz, CDCl$_3$) δ 7.19 (s, 1H), 1.74 (s, 6H), 1.58 (s, 9H).

Preparation 10 tert-Butyl 6,6-dimethyl-4-oxo-2-(4,4,5,5-tetramethyl-1,3,2-dioxaborolan-2-yl)thieno[2,3-c]pyrrole-5-carboxylate

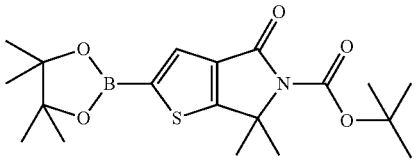 [SMILES: CC(C)(C)OC(=O)N1C(=O)c2cc(B3OC(C)(C)C(C)(C)O3)sc2C1(C)C]

Degas a mixture of tert-butyl 2-bromo-6,6-dimethyl-4-oxo-thieno[2,3-c]pyrrole-5-carboxylate (114 g, 329 mmol), bis(pinacolato)diboron (125 g, 494 mmol) and potassium acetate (97 g, 988 mmol) in 1,4-dioxane (1.6 L) with nitrogen for 10 minutes. Add (1,1'-bis(diphenylphosphino)ferrocene)palladium(II) chloride (5.38 g, 6.6 mmol) and heat the mixture at 90° C. for four hours. Cool the reaction to room temperature and filter through a CELITE® pad. Concentrate the filtrate and then treat the residue with 10% EtOAc in hexane. Collect the precipitate by vacuum filtration to give the title compound 65.8 g (40%). MS (m/z): 338 (M-isobutene+1).

Preparation 11 tert-Butyl 2-(2-chloropyrimidin-4-yl)-6,6-dimethyl-4-oxo-thieno[2,3-c]pyrrole-5-carboxylate

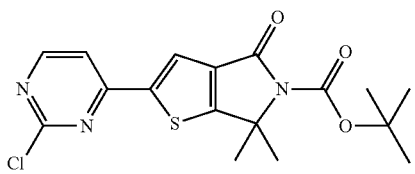 [SMILES: CC(C)(C)OC(=O)N1C(=O)c2cc(-c3ccnc(Cl)n3)sc2C1(C)C]

Synthetic Method 1:

Degas a mixture of tert-butyl 2-bromo-6,6-dimethyl-4-oxo-thieno[2,3-c]pyrrole-5-carboxylate (36 g, 104 mmol), bis(pinacolato)diboron (59.8 g, 235 mmol) and potassium acetate (33.2 g, 338 mmol) in 1,4-dioxane (520 mL) with nitrogen for 10 minutes. Add (1,1'-bis(diphenylphosphino)ferrocene)palladium(II) chloride (4.45 g, 5.5 mmol) and heat the mixture to 90° C. Heat the mixture at 90° C. for two hours. Cool the reaction to room temperature and stir for three hours. Add 2,4-dichloropyrimidine (22 g, 145 mmol) followed by a solution of potassium carbonate (20.4 g, 147 mmol) in water (83 mL). Degas the resulting mixture with nitrogen for 10 minutes. Add tetrakis(triphenylphosphine)palladium (1.59 g, 1.38 mmol) and heat the mixture to 90° C. for two hours. Cool the mixture to room temperature and filter through a pad of CELITE®. Wash the filtrate with three portions water and one portion of saturated NaCl. Concentrate the organics under reduced pressure. Purify the residue by silica gel column chromatography eluting with a gradient from 0-25% EtOAc in DCM to give the title compound 11 g (59%). MS (m/z): 324 (M-isobutene+1).

Synthetic Method 2

Degas a mixture of tert-butyl 6,6-dimethyl-4-oxo-2-(4,4,5,5-tetramethyl-1,3,2-dioxaborolan-2-yl)thieno[2,3-c]pyrrole-5-carboxylate (11.7 g, 30 mmol), 2,4-dichloropyrimidine (13 g, 89 mmol), potassium carbonate (20.4 g, 147 mmol), and water (50 mL) in 1,4-dioxane (100 mL) with nitrogen for 10 minutes. Add tetrakis(triphenylphosphine)palladium (2.58 g, 2.2 mmol) and heat the mixture to 87° C. for 1.5 hours. Cool the mixture to room temperature. Dilute the mixture with EtOAc (1 L) and wash the resulting solution with water and saturated NaCl. Dry the organic solution over anhydrous sodium sulfate, filter and concentrate the filtrate under reduced pressure. Treat the residue with 30% EtOAc in hexane (200 mL) and collect the resulting precipitate by vacuum filtration to give the title compound 7.6 g (67%). MS (m/z): 324 (M-isobutene+1).

Preparation 12

2-(2-Chloropyrimidin-4-yl)-6,6-dimethyl-5H-thieno[2,3-c]pyrrol-4-one

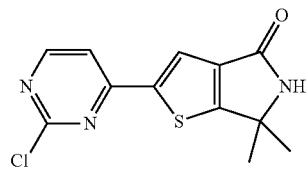 [SMILES: CC1(C)NC(=O)c2cc(-c3ccnc(Cl)n3)sc21]

Stir a mixture of tert-butyl 2-(2-chloropyrimidin-4-yl)-6,6-dimethyl-4-oxo-thieno[2,3-c]pyrrole-5-carboxylate (6.36 g, 16.7 mmol) and trifluoroacetic acid (25 mL) in DCM (25 mL) at room temperature for two hours. Concentrate the mixture under reduced pressure and dilute the residue with DCM. Partition the mixture with saturated aqueous sodium bicarbonate solution and collect the solids from the biphasic emulsion. Wash the solids with ether and dry under vacuum at 50° C. overnight to give the title compound 4.65 g (99%). MS (m/z): 280 (M+1).

Preparation 13

2-(2-Chloropyrimidin-4-yl)-6,6-dimethyl-5H-thieno[2,3-c]pyrrol-4-one hydrochloride

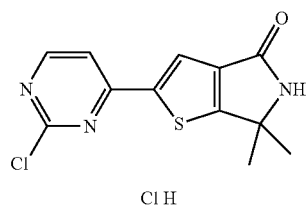 [SMILES: CC1(C)NC(=O)c2cc(-c3ccnc(Cl)n3)sc21 ; "Cl H"]

Heat a solution of tert-butyl 2-(2-chloropyrimidin-4-yl)-6,6-dimethyl-4-oxo-thieno[2,3-c]pyrrole-5-carboxylate (66.7 g, 176 mmol) and hydrogen chloride (4 M in 1,4-dioxane, 263 mL, 1054 mmol) in 1,4-dioxane (585 mL) at 30° C. for five hours. Remove the heating element and stir the mixture at room temperature overnight. Slowly add hexane (800 mL) to the reaction mixture. Stir the resulting slurry for 10 minutes and collect the solids by vacuum filtration. Dry the solid under vacuum to give the title compound 56 g (100%). MS (m/z): 280 (M+1).

Preparation 14

2-Bromo-6,6-dimethyl-5-(2-morpholinoethyl)thieno[2,3-c]pyrrol-4-one

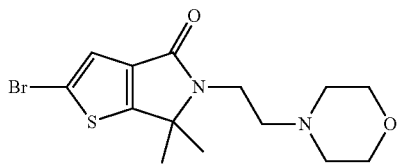 [SMILES: CC1(C)c2sc(Br)cc2C(=O)N1CCN1CCOCC1]

Add sodium hydroxide (160 g, 4 mol) to water (250 mL) and stir the mixture until a clear solution is produced. Add 1,4-dioxane (2 L) followed by 2-bromo-6,6-dimethyl-5H-thieno[2,3-c]pyrrol-4-one (215 g, 874 mmol), tetrabutylammonium iodide (300 g, 812 mmol) and 4-(2-chloroethyl)morpholine hydrochloride (300 g, 1564 mmol). Heat the mixture at 80° C. for one hour. Cool the reaction mixture to room temperature. Dilute the reaction with water (2 L) and extract the mixture with EtOAc (3×2 L). Dry the combined organic extracts over anhydrous sodium sulfate, filter and concentrate the filtrate under reduced pressure. Add DCM (2 L) and hexane (2 L) and wash the resulting organic solution with saturated NaCl (2×1 L). Concentrate the organic solution under reduced pressure to a minimum volume. Filter off the solids to give the title compound 180 g (57%). MS (m/z): 359/361 (M+1/M+3).

Preparation 15

2-Bromo-5-[2-[tert-butyl(dimethyl)silyl]oxyethyl]-6,6-dimethyl-thieno[2,3-c]pyrrol-4-one

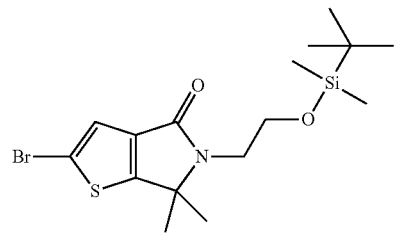 [SMILES: CC1(C)c2sc(Br)cc2C(=O)N1CCO[Si](C)(C)C(C)(C)C]

Treat a suspension of sodium hydride (60 wt % in mineral oil, 3.9 g, 97.5 mmol) in DMF (203 mL) at 0° C. with 2-bromo-6,6-dimethyl-5H-thieno[2,3-c]pyrrol-4-one (20 g, 81.3 mmol) followed by (2-bromoethoxy)-tert-butyldimethylsilane (23.3 g, 97.5 mmol). Stir the reaction at 0° C. for one hour. Remove the ice bath and stir the reaction mixture overnight. Quench the reaction mixture with saturated aqueous ammonium chloride and extract with EtOAc. Wash the organic solution with saturated NaCl. Dry the organic solution over anhydrous sodium sulfate, filter and concentrate the filtrate under reduced pressure. Purify the residue by silica gel column chromatography eluting with 20% EtOAc in hexane to give the title compound 26 g (79%). MS (m/z): 404/406 (M+1/M+3).

The following compound is prepared essentially by the method of Preparation 15.

| Prep. No. | Compound Name | Structure | MS (m/z): |
|---|---|---|---|
| 16 | 2'-Bromo-5'-(2-morpholinoethyl)spiro[cyclopropane-1,6'-thieno[2,3-c]pyrrole]-4'-one | 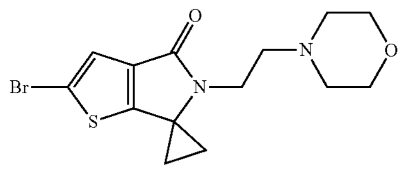 [SMILES: O=C1c2cc(Br)sc2C2(CC2)N1CCN1CCOCC1] | 357/359 (M + 1/M + 3) |

2-(2-Chloro-5-methyl-pyrimidin-4-yl)-6,6-dimethyl-5-(2-morpholinoethyl)thieno[2,3-c]pyrrol-4-one

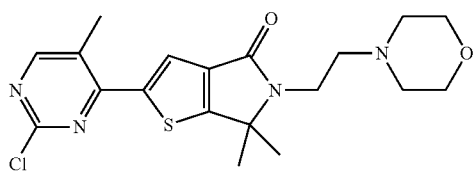 [SMILES: Cc1cnc(Cl)nc1-c1cc2c(s1)C(C)(C)N(CCN1CCOCC1)C2=O]

Degas a mixture of 2-bromo-6,6-dimethyl-5-(2-morpholinoethyl)thieno[2,3-c]pyrrol-4-one (5.76 g, 16 mmol), bis(pinacolato)diboron (4.88 g, 19.2 mmol) and potassium acetate (4.86 g, 48 mmol) in 1,4-dioxane (80 mL) with nitrogen for 20 minutes. Add (1,1'-bis(diphenylphosphino)ferrocene)palladium(II) chloride (668 mg, 0.80 mmol) and heat the mixture at 90° C. overnight. Cool the reaction to room temperature, concentrate the filtrate and then treat the residue with EtOAc. The precipitate is collected by vacuum filtration. To the solid (3.7 g) add 2,4-dichloro-5-methylpyrimidine (1.5 g, 9.1 mmol), 1,4-dioxane (50 mL), potassium carbonate (3.8 g, 27 mmol) and water (33 mL). Degas the resulting mixture with nitrogen for 20 minutes. Add tetrakis(triphenylphosphine)palladium (790 mg, 0.68 mmol) and heat the mixture to 90° C. for two hours. Cool the mixture to room temperature and dilute with EtOAc. Wash the organic solution with saturated NaCl. Dry the organic solution over anhydrous sodium sulfate, filter and concentrate the filtrate under reduced pressure. Purify the residue by silica gel column chromatography eluting with a gradient from 0-10% MeOH in EtOAc to give the title compound 1.82 g (19%). MS (m/z): 407 (M+1).

The following compounds are prepared essentially by the method of Preparation 17.

| Prep. No. | Compound Name | Structure | MS (m/z): |
|---|---|---|---|
| 18 | 2-(2,5-Dichloropyrimidin-4-yl)-6,6-dimethyl-5-(2-morpholinoethyl)thieno[2,3-c]pyrrol-4-one | 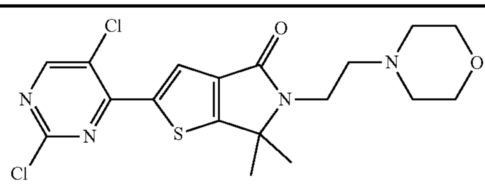 | 427 (M + 1) |
| 19 | 2-(2-Chloro-5-fluoro-pyrimidin-4-yl)-6,6-dimethyl-5-(2-morpholinoethyl)thieno[2,3-c]pyrrol-4-one | 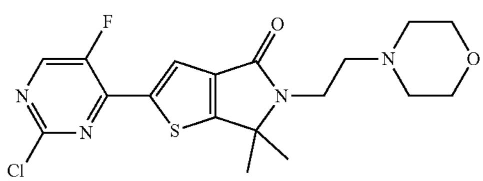 [SMILES: CC1(C)c2sc(-c3nc(Cl)ncc3F)cc2C(=O)N1CCN1CCOCC1] | 411 (M + 1) |
| 20 | 2-[2-Chloro-5-(trifluoromethyl)pyrimidin-4-yl]-6,6-dimethyl-5-(2-morpholinoethyl)thieno[2,3-c]pyrrol-4-one | 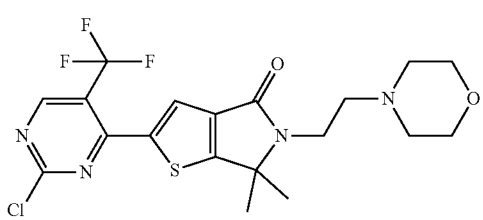 [SMILES: CC1(C)c2sc(-c3nc(Cl)ncc3C(F)(F)F)cc2C(=O)N1CCN1CCOCC1] | 461 (M + 1) |
| 21 | 5-[2-[tert-Butyl(dimethyl)silyl]oxyethyl]-2-(2-chloropyrimidin-4-yl)-6,6-dimethyl-thieno[2,3-c]pyrrol-4-one | 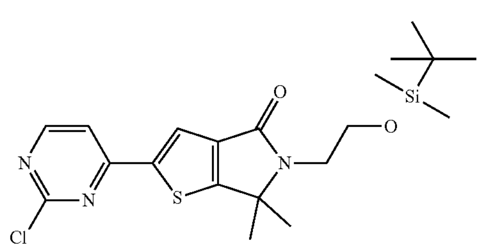 | 438 (M + 1) |

| Prep. No. | Compound Name | Structure | MS (m/z): |
|---|---|---|---|
| 22 | 2-(2-Chloropyrimidin-4-yl)-6,6-dimethyl-5-[2-(5-oxa-8-azaspiro[2.6]nonan-8-yl)ethyl]thieno[2,3-c]pyrrol-4-one | 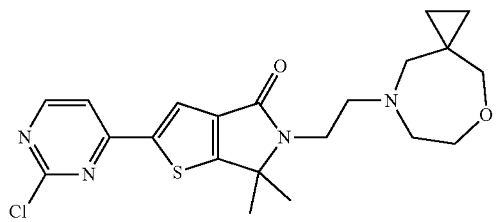 [SMILES: CC1(C)c2sc(-c3ccnc(Cl)n3)cc2C(=O)N1CCN1CCOCC2(CC2)C1] | 433 (M + 1) |
| 23 | 2'-(2-Chloropyrimidin-4-yl)-5'-(2-morpholinoethyl)spiro[cyclopropane-1,6'-thieno[2,3-c]pyrrole]-4'-one | 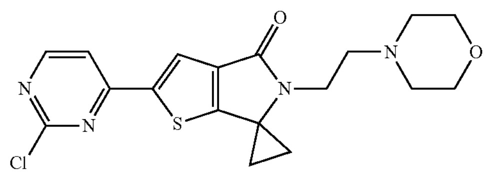 [SMILES: O=C1c2cc(-c3ccnc(Cl)n3)sc2C2(CC2)N1CCN1CCOCC1] | 391 (M + 1) |

Preparation 24

2-(2-Chloropyrimidin-4-yl)-6,6-dimethyl-5-(2-morpholinoethyl)thieno[2,3-c]pyrrol-4-one

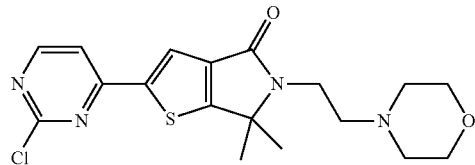 [SMILES: CC1(C)c2sc(-c3ccnc(Cl)n3)cc2C(=O)N1CCN1CCOCC1]

Synthetic Method 1:

Degas a mixture of 2-bromo-6,6-dimethyl-5-(2-morpholinoethyl)thieno[2,3-c]pyrrol-4-one (200 g, 557 mmol), bis(pinacolato)diboron (200 g, 788 mmol) and potassium acetate (200 g, 2038 mmol) in 1,4-dioxane (1 L) with nitrogen for 15 minutes. Add (1,1'-bis(diphenylphosphino)ferrocene)palladium(II) chloride (20 g, 27 mmol) and heat the mixture to 90° C. Heat the mixture at 90° C. for one hour. Cool the reaction to 50° C. and add potassium carbonate (250 g, 1809 mmol), 2,4-dichloropyrimidine (230 g, 1543 mmol) and water (300 mL). Heat the mixture at 90° C. for one hour. Cool the mixture to 35° C. and add water (700 mL). Extract the reaction mixture with DCM (2 L). The aqueous solution was back extracted with DCM (500 mL). Dry the combined organic solutions over anhydrous magnesium sulfate, filter and concentrate the filtrate under reduced pressure. Dilute the residue with 10% EtOAc in hexane (2 L) and stir for one hour. Decant the mother liquor and rinse the solids with hexane (500 mL). Dissolve the solids in DCM (300 mL) and slowly add hexanes (2 L). Collect the resulting solids by vacuum filtration and dry to give the title compound 150 g (65%). MS (m/z): 393 (M+1).

Synthetic Method 2:

Cool a mixture of 2-(2-chloropyrimidin-4-yl)-6,6-dimethyl-5H-thieno[2,3-c]pyrrol-4-one hydrochloride (10 g, 32 mmol) and tetrabutylammonium iodide (1.17 g, 3.16 mmol) in N-methylpyrrolidone (211 mL) to 0° C. using an ice water bath. Add sodium hydride (60 wt % in mineral oil, 5.06 g, 126.5 mmol) in portions. Stir the mixture at 0° C. for 10 minutes and then add 4-(2-bromoethyl)morpholine hydrobromide (13.9 g, 50.6 mmol). Remove the ice bath and stir the mixture for four hours. Quench the reaction mixture with saturated aqueous ammonium chloride and dilute the mixture with water (1 L). Extract the mixture with isopropyl acetate (4×700 mL). Dry the combined organic extracts over anhydrous sodium sulfate, filter and concentrate the filtrate under reduced pressure. Add 20% EtOAc in hexane and stir the mixture for one hour. Collect the solid by vacuum filtration and dry to give the title compound 8.6 g (69%). MS (m/z): 393 (M+1).

Synthetic Method 3:

Treat a solution of 2-(2-chloropyrimidin-4-yl)-6,6-dimethyl-5H-thieno[2,3-c]pyrrol-4-one (500 mg, 1.4 mmol) in DMF (14 mL) with sodium hydride (60 wt % in mineral oil, 129 mg, 3.2 mmol). Stir the mixture for 10 minutes and then add 4-(2-bromoethyl)morpholine hydrochloride (412 mg, 1.8 mmol). Stir the reaction mixture at room temperature overnight. Cool the mixture to 0° C. and add 4-(2-bromoethyl)morpholine hydrochloride (165 mg, 0.7 mmol) followed by sodium hydride (60 wt % in mineral oil, 14 mg, 0.4 mmol). Remove the ice bath and stir the mixture at room temperature overnight. Add sodium hydride (60 wt % in mineral oil, 14 mg, 0.4 mmol) and stir the resulting mixture at room temperature for five hours. Dilute the mixture with water and extract with EtOAc. Wash the organic extracts with 5% aqueous lithium chloride. Concentrate the organic solution under reduced pressure. Purify the residue by silica gel column chromatography eluting with a gradient from 0-10% MeOH in DCM to give the title compound 524 mg (93%). MS (m/z): 393 (M+1).

Preparation 25

5-[2-[tert-Butyl(dimethyl)silyl]oxyethyl]-6,6-dimethyl-2-[2-[(2-methylpyrazol-3-yl)amino]pyrimidin-4-yl]thieno[2,3-c]pyrrol-4-one

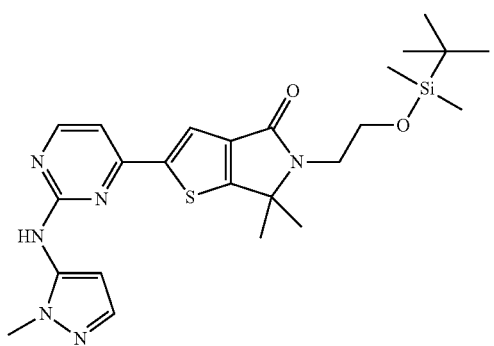 [SMILES: Cn1nccc1Nc1nccc(-c2cc3c(s2)C(C)(C)N(CCO[Si](C)(C)C(C)(C)C)C3=O)n1]

Degas a mixture of 5-[2-[tert-butyl(dimethyl)silyl]oxyethy]-2-(2-chloropyrimidin-4-yl)-6,6-dimethyl-thieno[2,3-c]pyrrol-4-one (6 g, 13.7 mmol), 2-methylpyrazol-3-amine (1.60 g, 16.4 mmol), cesium carbonate (8.92 g, 27.4 mmol), 4,5-bis(diphenylphosphino)-9,9-dimethylxanthene (790 mg, 1.37 mmol) and 1,4-dioxane (150 mL) with nitrogen for 10 minutes. Add palladium(II)acetate (610 mg, 2.74 mmol) and heat the mixture at 90° C. for 2.5 hours. Cool the mixture to room temperature and stir the mixture at room temperature overnight. Dilute the reaction mixture with 10% MeOH in DCM and stir the mixture for 15 minutes. Filter the mixture through CELITE® and wash the solids with 10% MeOH in DCM. Concentrate the filtrate under reduced pressure. Purify the residue by silica gel column chromatography eluting with a gradient from 60-100% EtOAc in DCM to give the title compound 5.73 g (84%). MS (m/z): 499 (M+1).

Preparation 26

2-Bromo-5-(2-hydroxyethyl)-6,6-dimethyl-thieno[2,3-c]pyrrol-4-one

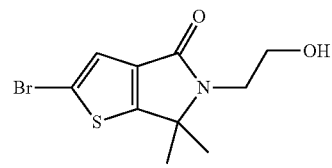

Treat 2-bromo-5-[2-[tert-butyl(dimethyl)siyl]-oxyethyl]-6,6-dimethyl-thieno[2,3-c]pyrrol-4-one (26 g, 64 mmol) in THF (40 mL) with acetic acid (120 mL) and water (40 mL). Stir the mixture at room temperature overnight. Concentrate the reaction mixture under reduced pressure. Dilute the residue with EtOAc and wash the resulting solution with saturated aqueous sodium bicarbonate followed by saturated NaCl. Dry the organic solution over anhydrous sodium sulfate, filter and concentrate the filtrate to give the title compound 18.97 g (100%). MS (m/z): 290/292 (M+1/M+3).

The following compound is prepared essentially by the method of Preparation 26.

| Prep. No. | Compound Name | Structure | Comments | MS (m/z): |
|---|---|---|---|---|
| 27 | 5-(2-Hydroxyethyl)-6,6-dimethyl-2-[2-[(2-methylpyrazol-3-yl)aminolpyrimidin-4-yl]thieno[2,3-c]pyrrol-4-one | 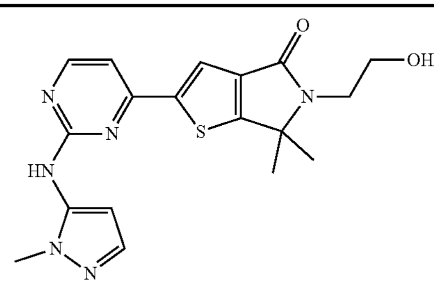 | 4N HCl dioxane is used. | 385 (M + 1) |

Preparation 28

2-(2-Bromo-6,6-dimethyl-4-oxo-thieno[2,3-c]pyrrol-5-yl)ethyl methanesulfonate

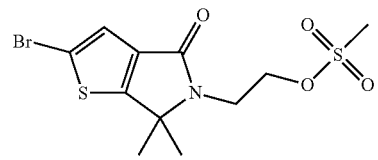 [SMILES: CC1(C)c2sc(Br)cc2C(=O)N1CCOS(C)(=O)=O]

Cool a solution of 2-bromo-5-(2-hydroxyethyl)-6,6-dimethyl-thieno[2,3-c]pyrrol-4-one (18.97 g, 65.4 mmol) in DCM (300 mL) to 0° C. Treat the mixture with triethylamine (13.7 mL, 98.1 mmol) and methanesulfonyl chloride (8.24 g, 71.9 mmol). Stir the mixture at 0° C. for two hours. Wash the solution with water and saturated NaCl. Dry the organic solution over anhydrous sodium sulfate, filter and concentrate the filtrate under reduced pressure. Purify the residue by silica gel column chromatography eluting with EtOAc to give the title compound 23.8 g (99%). MS (m/z): 368/370 (M+1/M+3).

The following compound is prepared essentially by the method of Preparation 28.

| Prep. No. | Compound Name | Structure | MS (m/z): |
|---|---|---|---|
| 29 | 2-[6,6-Dimethyl-2-[2-[(2-methylpyrazol-3-yl)amino]pyrimidin-4-yl]-4-oxo-thieno[2,3-c]pyrrol-5-yl]ethyl methanesulfonate | 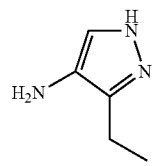 | 463 (M + 1) | and 4-dimethylaminopyridine (1.28 g, 10.5 mmol) in DCM (300 mL) with triethylamine (5.85 mL, 42 mmol) and stir the mixture at room temperature overnight. Concentrate the reaction mixture under reduced pressure. Purify the residue by silica gel column chromatography eluting with a gradient from 1-10% EtOAc in hexane to give the title compound 3.48 g (68%). $^1$H NMR (399.8 MHz, DMSO-$d_6$) δ 9.10 (s, 1H), 3.98 (s, 3H), 1.56 (s, 9H).

Preparation 30

3-Ethyl-4-nitro-1H-pyrazole

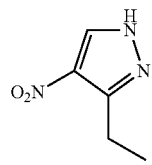

Dissolve 3-ethyl-1H-pyrazole (1 g, 10.4 mmol) in sulfuric acid (5 mL) and cool the mixture to a −5° C. Then add potassium nitrate (1.16 g, 11.4 mmol) in portions to the mixture. Stir the mixture overnight while allowing it to slowly warm to room temperature. Cool the mixture to 0° C. and quench slowly with ammonium hydroxide until the pH is approximately 10. Collect the resulting solid by vacuum filtration and wash with a small amount of water. Cool the filtrate to 0° C. and then collect the solid from the filtrate by vacuum filtration and wash with a small amount of water. Combine the solids and dissolve in DCM. Dry the organic solution over anhydrous sodium sulfate, filter and concentrate the filtrate under reduced pressure. Co-evaporate once with diethyl ether to give the title compound 1.34 g (91%). MS (m/z): 140 (M-1).

Preparation 31 tert-Butyl 3-methoxy-4-nitro-pyrazole-1-carboxylate

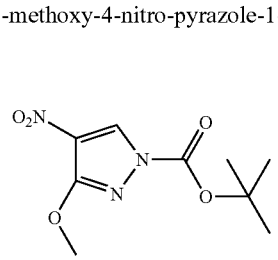

Treat a suspension of 5-methoxy-4-nitro-1H-pyrazole (3 g, 21 mmol), di-tert-butyl-dicarbonate (6.9 g, 31.6 mmol)

Preparation 32

3-Ethyl-1H-pyrazol-4-amine

Treat a suspension of palladium (5 wt % on carbon, 450 mg, 0.21 mmol) in EtOH (21 mL) with 3-ethyl-4-nitro-1H-pyrazole (300 mg, 2.13 mmol). Stir the resulting mixture under a hydrogen atmosphere for 6.5 hours. Filter the reaction mixture through CELITE® and rinse the solids with additional EtOH. Concentrate the filtrate under reduced pressure to give the title compound 240 g (99%). $^1$H NMR (400.1 MHz, CD$_3$CN) δ 7.02 (s, 1H), 2.54 (q, J=7 Hz, 3H), 1.17 (t, J=7 Hz, 9H).

The following compound is prepared essentially by the method of Preparation 32.

| Prep. No. | Compound Name | Structure | MS (m/z): |
|---|---|---|---|
| 33 | tert-Butyl 4-amino-3-methoxy-pyrazole-1-carboxylate | 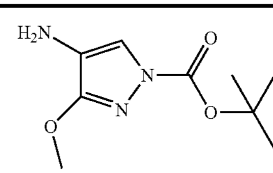 | 214 (M + 1) |

Preparation 34 tert-Butyl N-(2-cyclopropylpyrazol-3-yl)carbamate

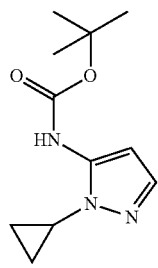 [SMILES: CC(C)(C)OC(=O)Nc1ccnn1C1CC1]

Cool a solution of 2-cyclopropylpyrazole-3-carboxylic acid (4 g, 26 mmol) in THF (35 mL) to 0° C. and then add triethylamine (5.5 mL, 39 mmol) followed by diphenylphosphonic azide (8.5 mL, 39 mmol). Stir the mixture for four hours while warm the reaction temperature slowly to room temperature. Add tert-butyl alcohol (4.99 mL) and heat the mixture at 70° C. for 18 hours. Concentrate the reaction mixture under reduced pressure. Purify the residue by silica gel column chromatography eluting with a gradient from 0-20% MeOH in DCM to give the title compound 5.39 g (92%). MS (m/z): 224 (M+1).

Preparation 35

2-Cyclopropylpyrazol-3-amine

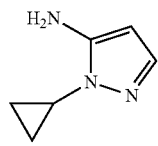

Treat a solution of tert-butyl N-(2-cyclopropylpyrazol-3-yl)carbamate (5.39 g, 24 mmol) in DCM (12 mL) with trifluoroacetic acid (16 mL, 213 mmol). Stir the solution at room temperature for one hour. Concentrate the reaction mixture under reduced pressure. Dissolve the residue in DCM and treat with saturated aqueous sodium bicarbonate solution until the pH of the aqueous phase persists at >7. Separate the phases and dry the organic phase over anhydrous sodium sulfate. Filter the mixture and concentrate the filtrate under reduced pressure. Concentrate the aqueous phase under reduced pressure. Combine the residues from the organic and aqueous phases and purify by reverse phase column chromatography (Column: 130 g C18; Mobile Phase: A) water, B) ACN; Gradient: 0-20% B). Concentrate the fractions and dissolve the residue in 25% MeOH in DCM. Filter the mixture and concentrate the filtrate under reduced pressure. Dissolve the residue in EtOAc and add water. Separate the layers and back extract the aqueous layer with EtOAc (8×100 mL). Concentrate the combined organic extract under reduced pressure to give the title compound 2.27 g (76%). $^1$H NMR (400.1 MHz, CD$_3$CN) δ 7.02 (d, J=2 Hz, 1H), 5.33 (d, J=2 Hz, 1H), 4.28 (bs, 2H), 3.10 (m, 1H), 0.96 (m, 4H).

Preparation 36

2-(Dibenzylamino)ethanol

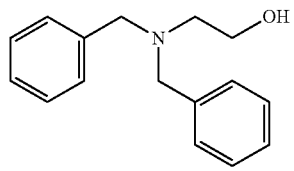 [SMILES: OCCN(Cc1ccccc1)Cc1ccccc1]

Treat a mixture of 2-(benzylamino)ethanol (0.95 mL, 6.6 mmol) in ACN (35 mL) with potassium carbonate (1.83 g, 13.2 mmol) followed by benzyl bromide (1.18 mL, 9.89 mmol). Heat the reactions mixture at 80° C. for 1.5 hours. Cool the reaction to room temperature and filter the mixture. Concentrate the filtrate under reduced pressure and purify the residue by silica gel column chromatography eluting with a gradient from 0-30% EtOAc in hexane to give the title compound 1.7 g (100%). MS (m/z): 242 (M+1).

Preparation 37

2-[2-(Dibenzylamino)ethoxy]-2,2-difluoro-acetic acid

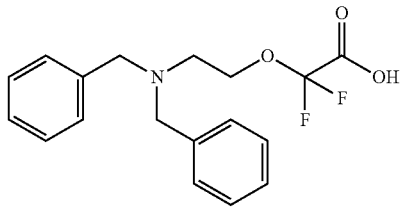 [SMILES: O=C(O)C(F)(F)OCCN(Cc1ccccc1)Cc1ccccc1]

Treat a solution of 2-(dibenzylamino)ethanol (1.5 g, 6.2 mmol) and sodium chloro-2,2-difluoro-acetic acid (950 mg, 6.19 mmol) in THF (12 mL) at 0° C. with sodium hydride (60 wt % in mineral oil, 500 mg, 12.5 mmol). Heat the reaction mixture to reflux overnight. Add additional sodium hydride (60 wt % in mineral oil, 120 mg, 3 mmol) to the reaction mixture and continue heating for an additional hour. Cool the reaction to room temperature and dilute with water. Extract the mixture with diethyl ether. Separate the layers and adjust the aqueous layer to pH 6 with 6 N hydrochloric acid. Extract the aqueous solution with EtOAc. Combine all organic solutions and dry over anhydrous sodium sulfate. Filter the mixture and concentrate the filtrate under reduced pressure to give the title compound 1.03 g (49%). MS (m/z): 336 (M+1).

Methyl
2-[2-(dibenzylamino)ethoxy]-2,2-difluoro-acetate

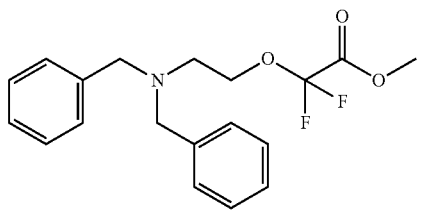 [SMILES: COC(=O)C(F)(F)OCCN(Cc1ccccc1)Cc1ccccc1]

Treat a solution of 2-[2-(dibenzylamino)ethoxy]-2,2-difluoro-acetic acid (100 mg, 0.298 mmol) in toluene (9 mL) and MeOH (2 mL) with (trimethylsilyl)diazomethane (2 M in hexane, 0.16 mL, 0.32 mmol) drop wise. Stir the mixture for 15 minutes at room temperature. Quench the reaction with acetic acid (0.1 mL) and concentrate the reaction mixture under reduced pressure to give the title compound 102 mg (98%). MS (m/z): 350 (M+1).

Preparation 39

4-Benzyl-2,2-difluoro-morpholin-3-one

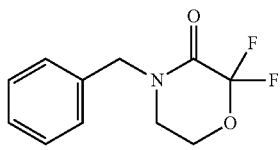 [SMILES: O=C1N(Cc2ccccc2)CCOC1(F)F]

Treat a suspension of palladium (10% on carbon, 50 mg, 0.141 mmol) in EtOH (15 mL) with methyl 2-[2-(dibenzylamino)ethoxy]-2,2-difluoro-acetate (485 mg, 1.39 mmol) in EtOH (15 mL). Stir the reaction mixture under a hydrogen atmosphere (balloon) at room temperature overnight. Filter the reaction mixture through CELITE® and concentrate the filtrate under reduced pressure to give the title compound 294 mg (93%). MS (m/z): 228 (M+1).

Preparation 40

4-Benzyl-2,2-difluoro-morpholine

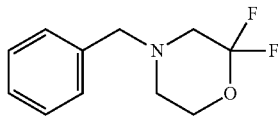 [SMILES: FC1(F)CN(Cc2ccccc2)CCO1]

Treat a solution of 4-benzyl-2,2-difluoro-morpholin-3-one (290 mg, 1.28 mmol) in THF (13 mL) with boron dimethyl sulfide complex (2 M in THF, 3.06 mL, 6.12 mmol). Heat the reaction mixture at 55° C. for 3.5 hours and then remove the heat and continue stirring overnight. Heat the reaction mixture to 55° C. for an additional two hours. Cool the reaction mixture to room temperature and quench by the dropwise addition of hydrochloric acid (6 N, 3.06 mL, 18.4 mmol). Heat the reaction mixture at 100° C. for one hour. Cool the mixture to room temperature and concentrate under reduced pressure. Dilute the mixture with water and adjust the pH to 12 with 2 N sodium hydroxide. Extract the mixture with EtOAc. Dry the organic extracts over anhydrous sodium sulfate, filter and concentrate the filtrate under reduced pressure to give the title compound 120 mg (44%). MS (m/z): 214 (M+1).

Preparation 41

2-Bromo-6,6-dimethyl-5-[2-(5-oxa-8-azaspiro[2.6]nonan-8-yl)ethyl]thieno[2,3-c]pyrrol-4-one

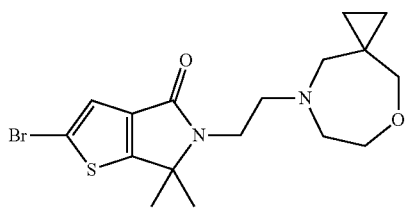 [SMILES: CC1(C)c2sc(Br)cc2C(=O)N1CCN1CCOCC2(CC2)C1]

Heat a mixture of 2-(2-bromo-6,6-dimethyl-4-oxo-thieno[2,3-c]pyrrol-5-yl)ethyl methanesulfonate (2.76 g, 6.9 mmol) and 5-oxa-8-azaspiro[2.6]nonane (2.18, 16.3 mmol) in DMF (33 mL) at 80° C. overnight. Cool the mixture to room temperature and dilute with EtOAc. Wash the organic solution with saturated NaCl (3×30 mL). Dry the organic solution over anhydrous sodium sulfate, filter and concentrate the filtrate under reduced pressure. Purify the residue by reverse phase column chromatography (Column: 100 g Gold C18; Mobile Phase: A) 0.1% formic acid in water, B) 0.1% formic acid in ACN; Gradient: 5% B for 5 minutes, 5%-50% B over 20 minutes; Flow Rate: 53 mL/minute) to give the title compound 3.6 g (85%). MS (m/z): 399/401 (M+1/M+3).

Preparation 42 tert-Butyl 4-[[4-[6,6-dimethyl-5-(2-morpholinoethyl)-4-oxo-thieno[2,3-c]pyrrol-2-yl]-5-methyl-pyrimidin-2-yl]amino]-3-methoxy-pyrazole-1-carboxylate

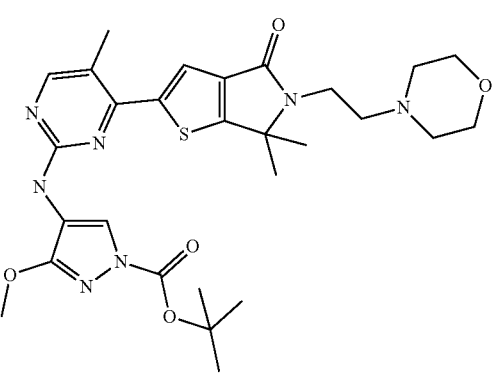 [SMILES: COc1nn(C(=O)OC(C)(C)C)cc1Nc1ncc(C)c(-c2cc3c(s2)C(C)(C)N(CCN2CCOCC2)C3=O)n1]

Degas a mixture of 2-(2-chloro-5-methyl-pyrimidin-4-yl)-6,6-dimethyl-5-(2-morpholinoethyl)thieno[2,3-c]pyrrol-4-one (250 mg, 0.61 mmol), tert-butyl 4-amino-3-methoxy-pyrazole-1-carboxylate (157 mg, 0.74 mmol), cesium carbonate (300 mg, 0.92 mmol), 4,5-bis(diphenylphosphino)-9,9-dimethylxanthene (71 mg, 0.12 mmol) and 1,4-dioxane (6.4 mL) with nitrogen for 15 minutes. Add palladium(II)acetate (14 mg, 0.0614 mmol) and heat the mixture at 110° C. overnight. Cool the mixture to room temperature and dilute with EtOAc. Wash the organic solution with saturated NaCl. Dry the organic solution over anhydrous sodium sulfate, filter and concentrate the filtrate under reduced pressure. Purify the residue by HPLC on a C18 column (Column: 150 g; Mobile Phase: A) 0.10% Formic Acid in Water, B) 0.10% Formic Acid in ACN; Gradient: 10-50% B; Flow Rate: 60 mL/min) to give the title compound 101 mg (28%). MS (m/z): 584 (M+1).

The following compounds are prepared essentially by the method of Preparation 42.

| Prep. No. | Compound Name | Structure | Comment | MS (m/z): |
|---|---|---|---|---|
| 43 | tert-Butyl 4-[[4-[6,6-dimethyl-5-(2-morpholinoethyl)-4-oxo-thieno[2,3-c]pyrrol-2-yl]pyrimidin-2-yl]amino]-3-methoxy-pyrazole-1-carboxylate | 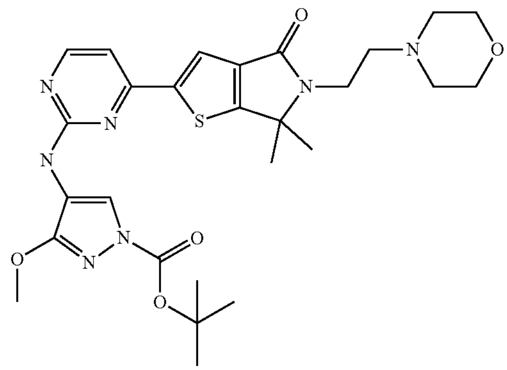 [SMILES: COc1nn(C(=O)OC(C)(C)C)cc1Nc1nccc(-c2cc3c(s2)C(C)(C)N(CCN2CCOCC2)C3=O)n1] | Catalyst: tris(dibenzylideneacetone) dipalladium (0) | 570 (M + 1) |
| 44 | tert-Butyl 4-[[4-6,6-dimethyl-5-(2-morpholinoethyl)-4-oxo-thieno[2,3-c]pyrrol-2-yl-5-fluoro-pyrimidin-2-yl]amino]-3-methoxy-pyrazole-1-carboxylate | 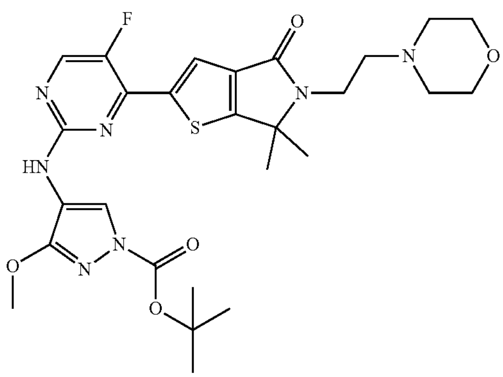 [SMILES: COc1nn(C(=O)OC(C)(C)C)cc1Nc1ncc(F)c(-c2cc3c(s2)C(C)(C)N(CCN2CCOCC2)C3=O)n1] | | 588 (M + 1) |
| 45 | tert-Butyl 5-cyclopropyl-4-[[4-[6,6-dimethyl-5-(2-morpholinoethyl)-4-oxo-thieno[2,3-c]pyrrol-2-yl]pyrimidin-2-yl]amino]pyrazole-1-carboxylate | 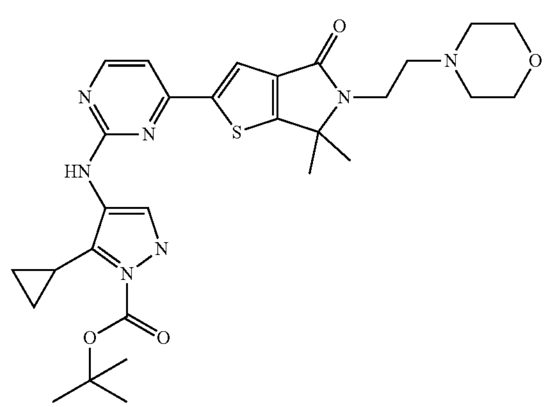 | | 580 (M + 1) |

EXAMPLE 1

6,6-Dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one

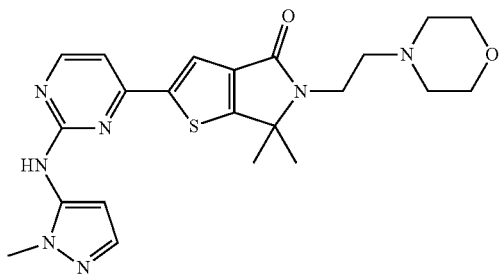

Synthetic Method 1:

Slowly add 2-methylpyrazol-3-amine (75 g, 772 mmol) to a suspension of sodium hydride (60 wt % in mineral oil, 30 g, 750 mmol) in N-methylpyrrolidone (500 mL). Stir the resulting mixture for 90 minutes. Add a solution of 2-(2-chloropyrimidin-4-yl)-6,6-dimethyl-5-(2-morpholinoethyl)thieno[2,3-c]pyrrol-4-one (145 g, 369 mmol) in N-methylpyrrolidone (200 mL). Cool the exothermic reaction to room temperature and pour the reaction into water (3 L). Adjust the pH to ~3 with concentrated hydrochloric acid (200 mL). Extract the mixture with DCM (4×2 L). Neutralize the aqueous layer using 5 M sodium hydroxide. Extract this aqueous solution with DCM (2×2 L). Combine these organic extracts and wash with water (2 L). Dry the organics over anhydrous sodium sulfate, filter and concentrate the filtrate under reduced pressure. Purify the residue on a silica gel plug (2 kg) eluting successively with DCM (2 L), 2.5% EtOH in DCM (2 L), 5% EtOH in DCM (2 L), 7.5% EtOH in DCM (2 L) and finally 10% EtOH in DCM (10 L). Concentrate the appropriate fractions under reduced pressure. Add EtOAc (1 L) and concentrate under reduced pressure. Add EtOAc (1 L) and concentrate under reduced pressure. Add EtOAc (500 mL) and hexane (500 mL). Collect the solid by vacuum filtration and wash the solid with hexane (500 mL). Dry the solid under vacuum at 50° C. to give the title compound 65.7 g (39%). MS (m/z): 454 (M+1).

Synthetic Method 2:

Degas a mixture of 2-(2-chloropyrimidin-4-yl)-6,6-dimethyl-5-(2-morpholinoethyl)thieno[2,3-c]pyrrol-4-one (20.8 g, 52.9 mmol), 2-methylpyrazol-3-amine (5.7 g, 58.2 mmol), cesium carbonate (37.9 g, 116.5 mmol), 4,5-bis(diphenylphosphino)-9,9-dimethylxanthene (2.6 g, 4.5 mmol) and 1,4-dioxane (529 mL) with nitrogen for 10 minutes. Add tris(dibenzylideneacetone)dipalladium(0) (2.4 g, 2.6 mmol) and heat the mixture to 85° C. for four hours. Cool the mixture to room temperature and filter the mixture through filter paper. Concentrate the filtrate under reduced pressure. Repeat the reaction starting with 8 g of 2-(2-chloropyrimidin-4-yl)-6,6-dimethyl-5-(2-morpholinoethyl)thieno[2,3-c]pyrrol-4-one and combine the two residues. Purify the residue by silica gel column chromatography (330 g) eluting with a gradient from 5-25% MeOH in (10% EtOAc in DCM). Pool the fractions and concentrate under reduced pressure. Re-purify the residue by silica gel column chromatography (330 g) eluting with a gradient from 5-25% MeOH in 10% EtOAc in DCM. Pool the fractions and concentrate under reduced pressure. Dissolve the residue in DCM (400 mL) and then add acetone (1 L). Slowly concentrate the mixture under reduced pressure to approximately 700 mL. Collect the solid by vacuum filtration to give the title compound 14.8 g (48%). MS (m/z): 454 (M+1).

Synthetic Method 3:

Degas a mixture of 2-(2-chloropyrimidin-4-yl)-6,6-dimethyl-5-(2-morpholinoethyl)thieno[2,3-c]pyrrol-4-one (250 mg, 0.64 mmol), 2-methylpyrazol-3-amine (124 mg, 1.3 mmol), cesium carbonate (622 mg, 1.9 mmol), 4,5-bis(diphenylphosphino)-9,9-dimethylxanthene (55 mg, 0.095 mmol) and 1,4-dioxane (6.4 mL) with nitrogen for 15 minutes. Add palladium(II)acetate (14.3 mg, 0.0636 mmol) and heat the mixture at 90° C. overnight. Cool the mixture to room temperature and filter the mixture through filter paper. Wash the solids with 10% MeOH in DCM. Concentrate the filtrate under reduced pressure. Repeat the reaction and combine the two residues. Purify the residue by HPLC on a C18 column (30×75 mm, 5 um, xbridge ODB) eluting with a 85 mL/minute gradient from 9-28% ACN in 10 mM ammonium carbonate (pH 10) in water. Pool the fractions and concentrate under reduced pressure to remove the ACN. Lyophilize the aqueous solution to give the title compound 100 mg (18%). MS (m/z): 454 (M+1).

The following compounds are prepared essentially by the synthetic method 3 of Example 1.

| Ex. No. | Chemical name | Structure | Physical data MS (m/z): |
|---|---|---|---|
| 2 | 6,6-Dimethyl-2-{5-methyl-2-[(1-methyl-1H-pyrazol-5-yl)amino]pyrimidin-4-yl}-5-[2-(morpholin-4-yl)ethyl]-5,6-dihydro-4H-thieno [2,3-c]pyrrol-4-one | 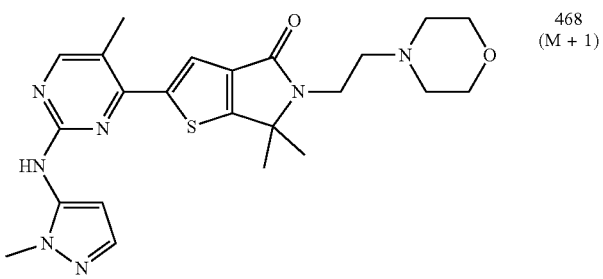 | 468 (M + 1) |

-continued

| Ex. No. | Chemical name | Structure | Physical data MS (m/z): |
|---|---|---|---|
| 3 | 4-[(4-{6,6-Dimethyl-5-[2-(morpholin-4-yl)ethyl]-4-oxo-5,6-dihydro-4H-thieno[2,3-c]pyrrol-2-yl}pyrimidin-2-yl)amino]-1-methyl-1H-pyrazole-3-carbonitrile | 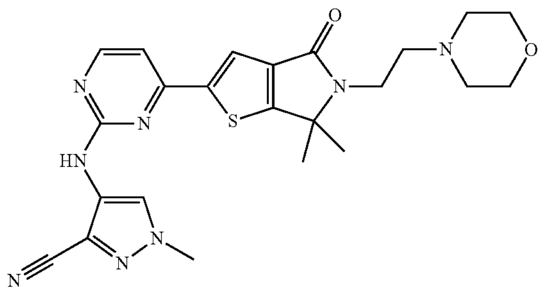 [SMILES: Cn1cc(Nc2nccc(-c3cc4c(s3)C(C)(C)N(CCN3CCOCC3)C4=O)n2)c(C#N)n1] | 479 (M + 1) |
| 4 | 6,6-Dimethyl-2-{2-[(1-methyl-1H-pyrazol-5-yl)amino]pyrimidin-4-yl}-5-[2-(5-oxa-8-azaspiro[2.6]non-8-yl)ethyl]-5,6-dihydro-4H-thieno[2,3-c]pyrrol-4-one | 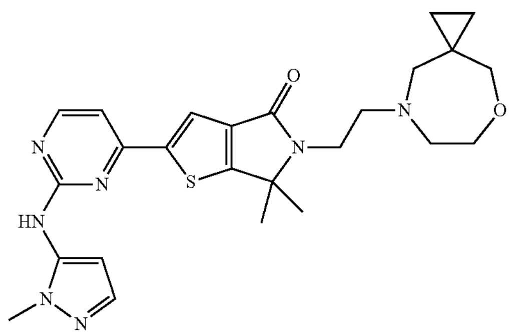 [SMILES: Cn1nccc1Nc1nccc(-c2cc3c(s2)C(C)(C)N(CCN2CCOCC4(CC4)C2)C3=O)n1] | 494 (M + 1) |
| 5 | 2'-{2-[(1-Methyl-1H-pyrazol-5-yl)amino]pyrimidin-4-yl}-5'-[2-(morpholin-4-yl)ethyl]spiro[cyclopropane-1,6'-thieno[2,3-c]pyrrol]-4'(5'H)-one | 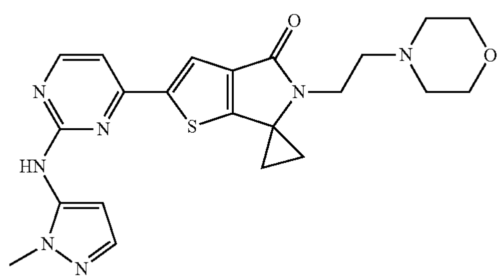 [SMILES: Cn1nccc1Nc1nccc(-c2cc3c(s2)C2(CC2)N(CCN2CCOCC2)C3=O)n1] | 452 (M + 1) |
| 6 | 6,6-Dimethyl-2-{2-[(1-methyl-1H-pyrazol-5-yl)amino]-5-(trifluoromethyl)pyrimidin-4-yl}-5-[2-(morpholin-4-yl)ethyl]-5,6-dihydro-4H-thieno[2,3-c]pyrrol-4-one | 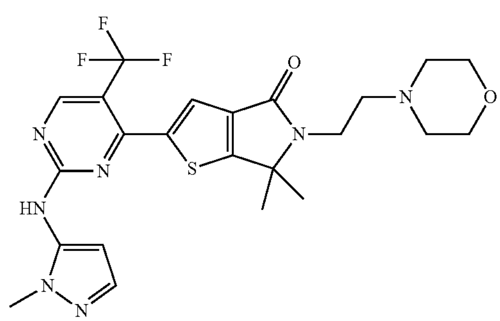 [SMILES: Cn1nccc1Nc1ncc(C(F)(F)F)c(-c2cc3c(s2)C(C)(C)N(CCN2CCOCC2)C3=O)n1] | 522 (M + 1) |
| 7 | 2-{2-[(3-Methoxy-1-methyl-1H-pyrazol-4-yl)amino]-5-methylpyrimidin-4-yl}-6,6-dimethyl-5-[2-(morpholin-4-yl)ethyl]-5,6-dihydro-4H-thieno[2,3-c]pyrrol-4-one | 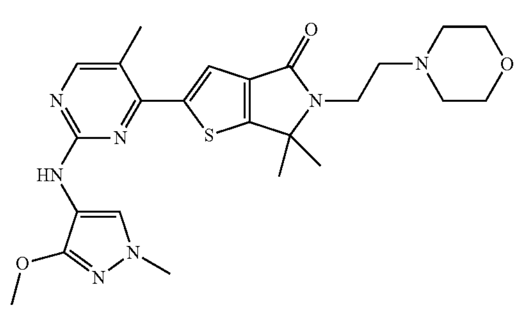 [SMILES: COc1nn(C)cc1Nc1ncc(C)c(-c2cc3c(s2)C(C)(C)N(CCN2CCOCC2)C3=O)n1] | 498 (M + 1) |

-continued

| Ex. No. | Chemical name | Structure | Physical data MS (m/z): |
|---|---|---|---|
| 8 | 2-{2-[(2,3-Dimethylpyridin-4-yl)amino]pyrimidin-4-yl}-6,6-dimethyl-5-[2-(morpholin-4-yl)ethyl]-5,6-dihydro-4H-thieno[2,3-c]pyrrol-4-one | 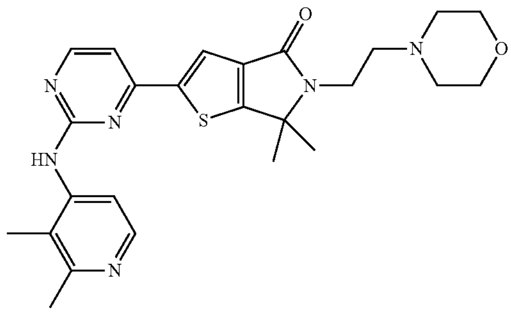 [SMILES: Cc1nccc(Nc2nccc(-c3cc4c(s3)C(C)(C)N(CCN3CCOCC3)C4=O)n2)c1C] | 479 (M + 1) |
| 9 | 6,6-Dimethyl-2-{2-[(1-methyl-1H-pyrazol-4-yl)amino]pyrimidin-4-yl-5-[2-(morpholin-4-yl)ethyl]-5,6-dihydro-4H-thieno[2,3-c]pyrrol-4-one | 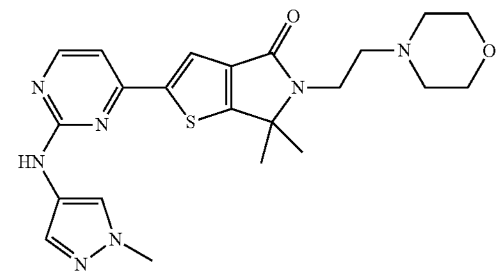 [SMILES: Cn1cc(Nc2nccc(-c3cc4c(s3)C(C)(C)N(CCN3CCOCC3)C4=O)n2)cn1] | 454 (M + 1) |
| 10 | 2-{2-[(4-Fluoro-2-methylphenyl)amino]-5-methylpyrimidin-4-yl}-6,6-dimethyl-5-[2-(morpholin-4-yl)ethyl]-5,6-dihydro-4H-thieno[2,3-c]pyrrol-4-one | 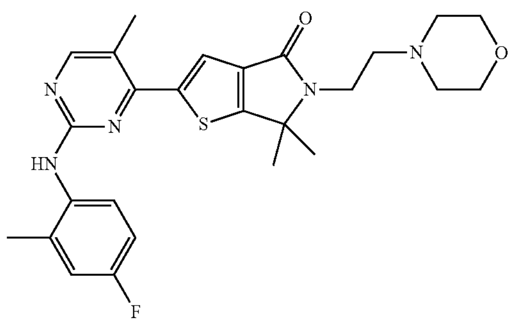 [SMILES: Cc1cc(F)ccc1Nc1ncc(C)c(-c2cc3c(s2)C(C)(C)N(CCN2CCOCC2)C3=O)n1] | 496 (M + 1) |
| 11 | 6,6-Dimethyl-2-[5-methyl-2-(pyrimidin-4-ylamino)pyrimidin-4-yl]-5-[2-(morpholin-4-yl)ethyl]-5,6-dihydro-4H-thieno[2,3-c]pyrrol-4-one | 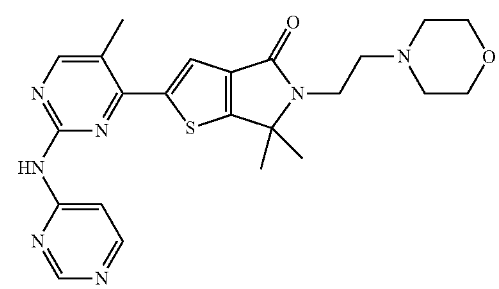 [SMILES: Cc1cnc(Nc2ccncn2)nc1-c1cc2c(s1)C(C)(C)N(CCN1CCOCC1)C2=O] | 466 (M + 1) |
| 12 | 2-{2-[(2,3-Dimethylpyridin-4-yl)amino]-5-methylpyrimidin-4-yl}-6,6-dimethyl-5-[2-(morpholin-4-yl)ethyl]-5,6-dihydro-4H-thieno[2,3-c]pyrrol-4-one | 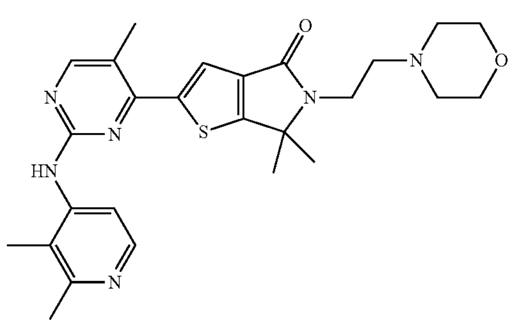 [SMILES: Cc1cnc(Nc2ccnc(C)c2C)nc1-c1cc2c(s1)C(C)(C)N(CCN1CCOCC1)C2=O] | 493 (M + 1) |

| Ex. No. | Chemical name | Structure | Physical data MS (m/z): |
|---|---|---|---|
| 13 | 4-[(4-{6,6-Dimethyl-5-[2-(morpholin-4-yl)ethyl]-4-oxo-5,6-dihydro-4H-thieno[2,3-c]pyrrol-2-yl}pyrimidin-2-yl)amino]pyridine-3-carbonitrile | 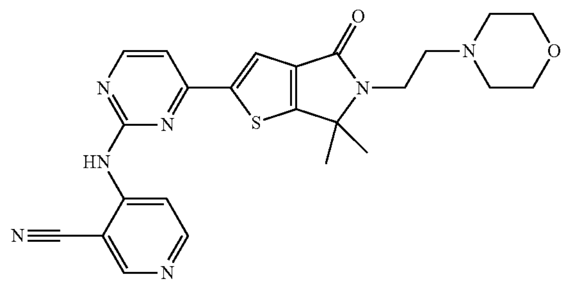 [SMILES: CC1(C)c2sc(-c3ccnc(Nc4ccncc4C#N)n3)cc2C(=O)N1CCN1CCOCC1] | 476 (M + 1) |
| 14 | 2-{5-Chloro-2-[(1-methyl-1H-pyrazol-5-yl)amino]pyrimidin-4-yl}-6,6-dimethyl-5-[2-(morpholin-4-yl)ethyl]-5,6-dihydro-4H-thieno[2,3-c]pyrrol-4-one | 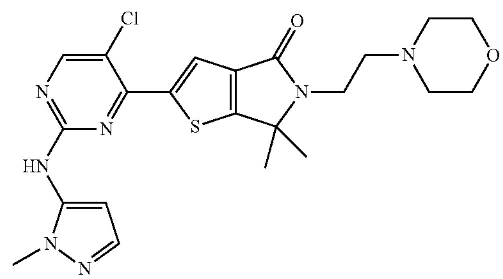 [SMILES: Cn1nccc1Nc1ncc(Cl)c(-c2cc3c(s2)C(C)(C)N(CCN2CCOCC2)C3=O)n1] | 488 (M + 1) |
| 15 | 2-{5-Fluoro-2-[(1-methyl-1H-pyrazol-5-yl)amino]pyrimidin-4-yl}-6,6-dimethyl-5-[2-(morpholin-4-yl)ethyl]-5,6-dihydro-4H-thieno[2,3-c]pyrrol-4-one | 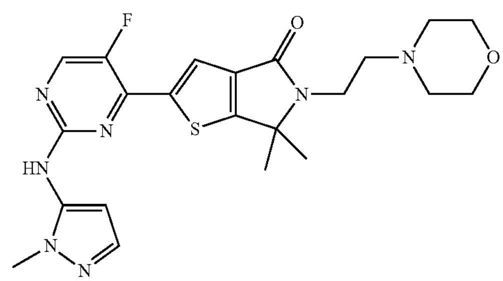 [SMILES: Cn1nccc1Nc1ncc(F)c(-c2cc3c(s2)C(C)(C)N(CCN2CCOCC2)C3=O)n1] | 472 (M + 1) |
| 16 | 4-[(4-{6,6-Dimethyl-5-[2-(morpholin-4-yl)ethyl]-4-oxo-5,6-dihydro-4H-thieno[2,3-c]pyrrol-2-yl}-5-fluoropyrimidin-2-yl)amino]-1-methyl-1H-pyrazole-3-carbonitrile | 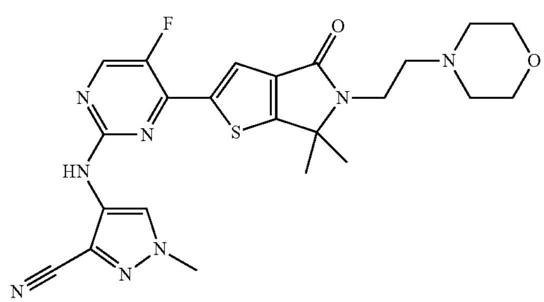 [SMILES: Cn1cc(Nc2ncc(F)c(-c3cc4c(s3)C(C)(C)N(CCN3CCOCC3)C4=O)n2)c(C#N)n1] | 497 (M + 1) |
| 17* | 2-{2-[(1,3-Dimethyl-1H-pyrazol-5-yl)amino]pyrimidin-4-yl}-6,6-dimethyl-5-[2-(morpholin-4-yl)ethyl]-5,6-dihydro-4H-thieno[2,3-c]pyrrol-4-one | 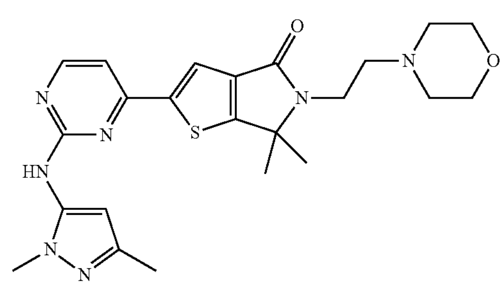 [SMILES: Cc1cc(Nc2nccc(-c3cc4c(s3)C(C)(C)N(CCN3CCOCC3)C4=O)n2)n(C)n1] | 468 (M + 1) |

| Ex. No. | Chemical name | Structure | Physical data MS (m/z): |
|---|---|---|---|
| 18 | 2-{2-[(2,4-Difluorophenyl)amino]-5-methylpyrimidin-4-yl}-6,6-dimethyl-5-[2-(morpholin-4-yl)ethyl]-5,6-dihydro-4H-thieno[2,3-c]pyrrol-4-one | 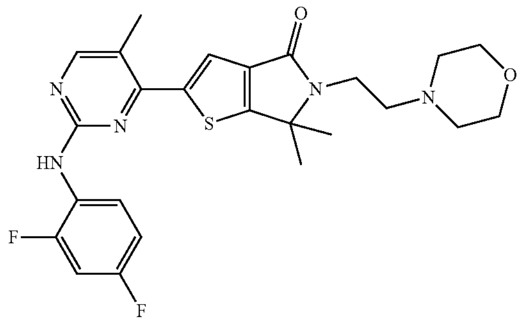 [SMILES: Cc1cnc(Nc2ccc(F)cc2F)nc1-c1cc2c(s1)C(C)(C)N(CCN1CCOCC1)C2=O] | 500 (M + 1) |
| 19 | 2-{2-[(2,4-Difluorophenyl)amino]pyrimidin-4-yl}-6,6-dimethyl-5-[2-(morpholin-4-yl)ethyl]-5,6-dihydro-4H-thieno[2,3-c]pyrrol-4-one | 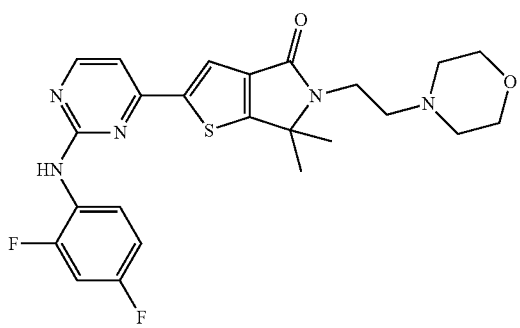 [SMILES: CC1(C)c2sc(-c3ccnc(Nc4ccc(F)cc4F)n3)cc2C(=O)N1CCN1CCOCC1] | 486 (M + 1) |

*Use [(4,5-bis(diphenylphosphino)-9,9-dimethylxanthene)-2-(2'-amino-1,1'-biphenyl)]palladium(II) methanesulfonate as ligand.

EXAMPLE 20

4-[(4-{6,6-Dimethyl-5-[2-(morpholin-4-yl)ethyl]-4-oxo-5,6-dihydro-4H-thieno[2,3-c]pyrrol-2-yl}pyrimidin-2-yl)amino]-1H-pyrazole-5-carbonitrile

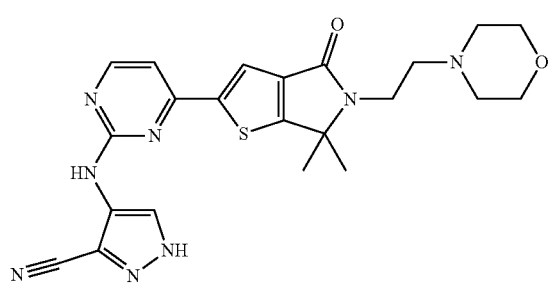 [SMILES: CC1(C)c2sc(-c3ccnc(Nc4c[nH]nc4C#N)n3)cc2C(=O)N1CCN1CCOCC1]

Heat a solution of 2-(2-chloropyrimidin-4-yl)-6,6-dimethyl-5-(2-morpholinoethyl)thieno[2,3-c]pyrrol-4-one (350 mg, 0.89 mmol), 4-amino-1H-pyrazole-5-carbonitrile (116 mg, 1.07 mmol), potassium carbonate (320 mg, 2.32 mmol), 2-(di-tert-butylphosphino)-2',4',6'-triisopropyl-3,6-dimethoxy-1,1'-biphenyl (87 mg, 0.18 mmol), tert-butyl alcohol (2.3 mL) and acetic acid (one drop) at 90° C. for two hours. Cool the mixture to room temperature. Dilute the mixture with 10% MeOH in DCM and filter the solution through a CELITE® column with a small amount of silica gel on top. Wash the column with 10% MeOH in DCM and concentrate the filtrate under reduced pressure. Purify the residue by reverse phase column chromatography (Column: C18, 275 g Gold; Mobile Phase: A) 10 mM Ammonium bicarbonate in water with 5% MeOH, B) ACN; Gradient: 10% B for 5 minutes, gradient to 40% B over 25 minutes; Flow Rate: 125 mL/min) to give the title compound 240 mg (58%). MS (m/z): 465 (M+1).

The following compound is prepared essentially by the method of Example 20.

| Ex. No. | Chemical name | Structure | Physical data MS (m/z): |
|---|---|---|---|
| 21 | 6,6-Dimethyl-5-[2-(morpholin-4-yl)ethyl]-2-[2-(1H-1,2,3-triazol-5-4-yl]-5,6-dihydro-4H-thieno[2,3-c]pyrrol-4-one | 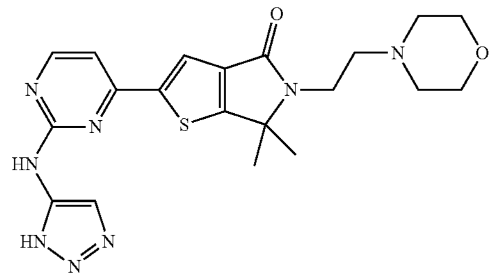 [SMILES: CC1(C)c2sc(-c3ccnc(Nc4cnn[nH]4)n3)cc2C(=O)N1CCN1CCOCC1] | 441 (M + 1) |

EXAMPLE 22

6,6-Dimethyl-2-{2-[(5-methyl-1H-pyrazol-4-yl)amino]pyrimidin-4-yl}-5-[2-(morpholin-4-yl)ethyl]-5,6-dihydro-4H-thieno[2,3-c]pyrrol-4-one

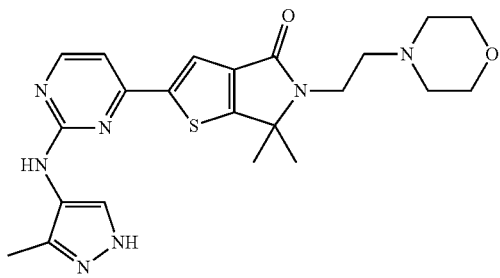 [SMILES: Cc1n[nH]cc1Nc1nccc(-c2cc3c(s2)C(C)(C)N(CCN2CCOCC2)C3=O)n1]

Purge a mixture of 2-(2-chloropyrimidin-4-yl)-6,6-dimethyl-5-(2-morpholinoethyl)thieno[2,3-c]pyrrol-4-one (230 mg, 0.59 mmol), 3-methyl-1H-pyrazol-4-amine (142 mg, 0.73 mmol), chloro[2-(di-tert-butylphosphino)-2',4',6'-triisopropyl-1,1'-biphenyl][2-(2-aminoethyl)phenyl)]palladium(II) (8 mg, 0.012 mmol), 2-di-tert-butylphosphino-2',4',6'-triisopropylbiphenyl (5 mg, 0.012 mmol) and sodium tert-butoxide (118 mg, 1.2 mmol) three times with nitrogen. Add tert-butyl alcohol (2 mL), seal the reaction and stir the mixture at room temperature for 1.5 hours. Treat the reaction mixture with EtOAc and stir the mixture overnight. Concentrate under reduced pressure. Dissolve the residue in EtOAc and wash the organic solution with saturated aqueous ammonium chloride. Back extract the aqueous layer twice with EtOAc. Dry the combine organic extracts over anhydrous sodium sulfate, filter and concentrate the filtrate under reduced pressure. Purify the residue by silica gel column chromatography eluting with a gradient from 0-10% MeOH in DCM to give the title compound 164 mg (62%). MS (m/z): 454 (M+1).

The following compounds are prepared essentially by the method of Example 22.

| Ex. No. | Chemical name | Structure | Physical data MS (m/z): |
|---|---|---|---|
| 23 | 2-{2-[(1-Cyclopropyl-1H-pyrazol-5-yl)amino]pyrimidin-4-yl}-6,6-dimethyl-5-[2-(morpholin-4-yl)ethyl]-5,6-dihydro-4H-thieno[2,3-c]pyrrol-4-one | 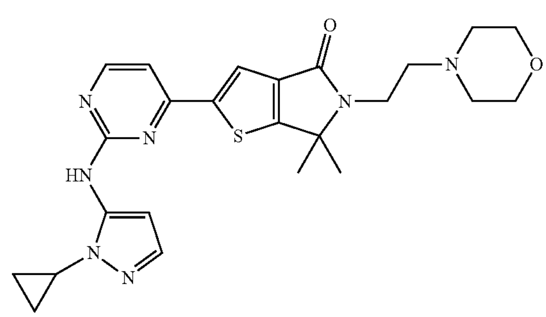 [SMILES: CC1(C)c2sc(-c3ccnc(Nc4ccnn4C4CC4)n3)cc2C(=O)N1CCN1CCOCC1] | 480 (M + 1) |

| Ex. No. | Chemical name | Structure | Physical data MS (m/z): |
|---|---|---|---|
| 24 | 2-{2-[(5-Ethyl-1H-pyrazol-4-yl)amino]pyrimidin-4-yl}-6,6-dimethyl-5-[2-(morpholin-4-yl)ethyl]-5,6-dihydro-4H-thieno[2,3-c]pyrrol-4-one | 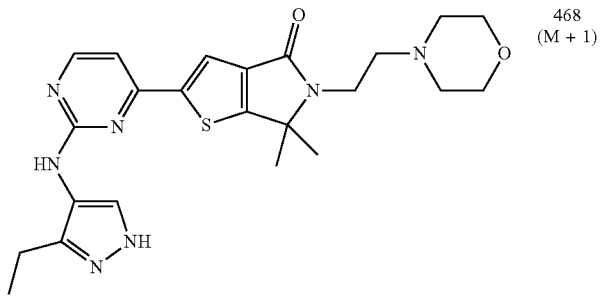 | 468 (M + 1) |

EXAMPLE 25

6,6-Dimethyl-2-{2-[(1-methyl-1H-pyrazol-5-yl)amino]pyrimidin-4-yl}-5-[2-(thiomorpholin-4-yl)ethyl]-5,6-dihydro-4H-thieno[2,3-c]pyrrol-4-one

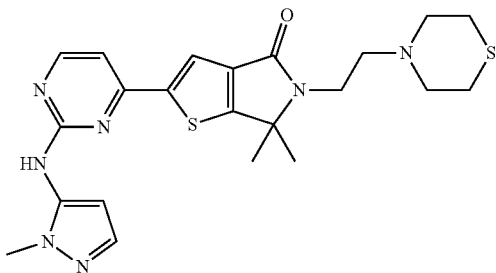 [SMILES: Cn1nccc1Nc1nccc(-c2cc3c(s2)C(C)(C)N(CCN2CCSCC2)C3=O)n1]

Heat a mixture of 2-[6,6-dimethyl-2-[2-[(2-methylpyrazol-3-yl)amino]pyrimidin-4-yl]-4-oxo-thieno[2,3-c]pyrrol-5-yl]ethyl methanesulfonate (260 mg, 0.56 mmol), thiomorpholine (116 mg, 1.12 mmol) and triethylamine (0.18 mL, 0.38 mmol) in ACN (2 mL) at 60° C. overnight. Cool the mixture to room temperature and filter the solution through CELITE®. Wash the solids with 10% MeOH in DCM and concentrate the filtrate under reduced pressure. Purify the residue by reverse phase column chromatography (Column: C18, 275 g Gold; Mobile Phase: A) 10 mM Ammonia in 5% MeOH in water, B) ACN; Gradient: 10% B for 5 minutes, gradient to 10-65% B over 25 mins; Flow Rate: 200 mL/min) to give the title compound 170 mg (64%). MS (m/z): 470 (M+1).

The following compounds are prepared essentially by the method of Example 25.

| Ex. No. | Chemical name | Structure | Physical data MS (m/z): |
|---|---|---|---|
| 26 | 6,6-Dimethyl-2-{2-[(1-methyl-1H-pyrazol-5-yl)amino]pyrimidin-4-yl}-5-[2-(2,2,6,6-tetrafluoromorpholin-4-yl)ethyl]-5,6-dihydro-4H-thieno [2,3-c]pyrrol-4-one | 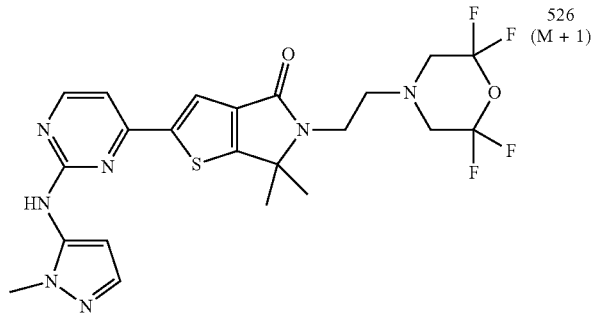 | 526 (M + 1) |

-continued

| Ex. No. | Chemical name | Structure | Physical data MS (m/z): |
|---|---|---|---|
| 27 | 6,6-Dimethyl-2-{2-[(1-methyl-1H-pyrazol-5-yl)amino]pyrimidin-4-yl}-5-[2-(1,4-oxazepan-4-yl)ethyl]-5,6-dihydro-4H-thieno[2,3-c]pyrrol-4-one | 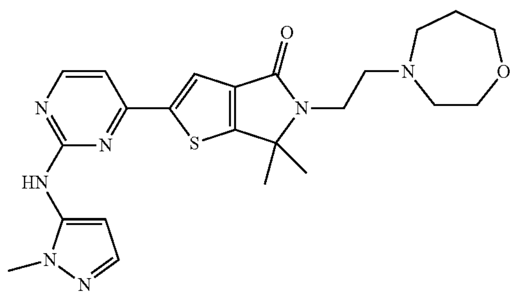 [SMILES: Cn1nccc1Nc1nccc(-c2cc3c(s2)C(C)(C)N(CCN2CCCOCC2)C3=O)n1] | 468 (M + 1) |
| 28 | 6,6-Dimethyl-2-{2-[(1-methyl-1H-pyrazol-5-yl)amino]pyrimidin-4-yl}-5-[2-(8-oxa-3-azabicyclo[3.2.1]oct-3-yl)ethyl]-5,6-dihydro-4H-thieno[2,3-c]pyrrol-4-one | 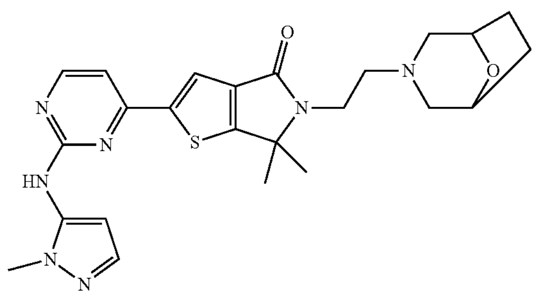 [SMILES: Cn1nccc1Nc1nccc(-c2cc3c(s2)C(C)(C)N(CCN2CC4CCC(C2)O4)C3=O)n1] | 480 (M + 1) |
| 29 | 5-[2-(3,3-Difluoropyrrolidin-1-yl)ethyl]-6,6-dimethyl-2-{2-[(1-methyl-1H-pyrazol-5-yl)amino]pyrimidin-4-yl}-5,6-dihydro-4H-thieno[2,3-c]pyrrol-4-one | 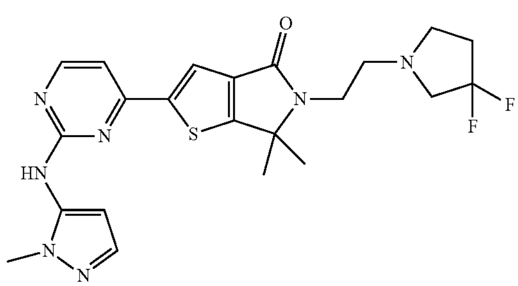 [SMILES: Cn1nccc1Nc1nccc(-c2cc3c(s2)C(C)(C)N(CCN2CCC(F)(F)C2)C3=O)n1] | 474 (M + 1) |
| 30 | 6,6-Dimethyl-2-{2-[(1-methyl-1H-pyrazol-5-yl)amino]pyrimidin-4-yl}-5-[2-(2-oxa-5-azabicyclo[4.1.0]hept-5-yl)ethyl]-5,6-dihydro-4H-thieno[2,3-c]pyrrol-4-one | 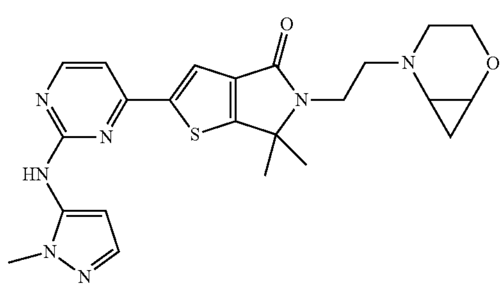 [SMILES: Cn1nccc1Nc1nccc(-c2cc3c(s2)C(C)(C)N(CCN2CCOC4CC42)C3=O)n1] | 466 (M + 1) |
| 31 | 6,6-Dimethyl-5-{2-[(3R)-3-methylmorpholin-4-yl]ethyl}-2-{2-[(1-methyl-1H-pyrazol-5-yl)amino]pyrimidin-4-yl}-5,6-dihydro-4H-thieno[2,3-c]pyrrol-4-one | Chiral | 468 (M + 1) |

EXAMPLE 32

5-[2-(2,2-Difluoromorpholin-4-yl)ethyl]-6,6-dimethyl-2-{2-[(1-methyl-1H-pyrazol-5-yl)amino]pyrimidin-4-yl}-5,6-dihydro-4H-thieno[2,3-c]pyrrol-4-one

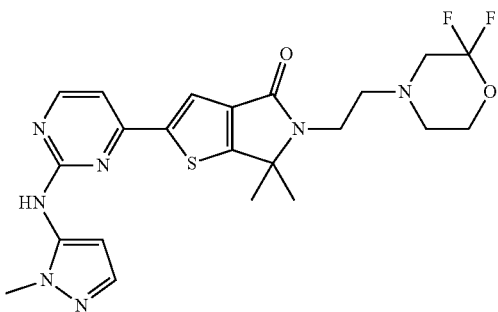 [SMILES: Cn1nccc1Nc1nccc(-c2cc3c(s2)C(C)(C)N(CCN2CCOC(F)(F)C2)C3=O)n1]

Treat a suspension of palladium hydroxide (20% on carbon, 63 mg, 0.09 mmol) in EtOAc (5 mL) with 4-benzyl-2,2-difluoro-morpholine (95 mg, 0.45 mmol) in EtOAc (5 mL). Stir the reaction mixture under a hydrogen atmosphere (balloon) at room temperature for five hours. Filter the reaction mixture through CELITE® and isolate the filtrate. To the filtrate, add triethylamine (0.11 mL, 0.79 mmol) and 2-[6,6-dimethyl-2-[2-[(2-methylpyrazol-3-yl)amino]pyrimidin-4-yl]-4-oxo-thieno[2,3-c]pyrrol-5-yl]ethyl methanesulfonate (306 mg, 0.66 mmol). Heat the mixture at 80° C. for one hour. Add ACN (15 mL) and heat the mixture at 80° C. for two days. Cool the reaction mixture to room temperature and concentrate under reduced pressure. Purify the residue by silica gel column chromatography eluting with a gradient from 0-10% MeOH in EtOAc. Concentrate the fractions under reduced pressure. Re-purify the residue by silica gel column chromatography eluting with a gradient from 50-100% EtOAc in hexane followed by a second gradient from 0-10% MeOH in EtOAc to give the title compound 47 mg (30%). MS (m/z): 490 (M+1).

EXAMPLE 33

5-[2-(6,6-Difluoro-1,4-oxazepan-4-yl)ethyl]-6,6-dimethyl-2-{2-[(1-methyl-1H-pyrazol-5-yl)amino]pyrimidin-4-yl}-5,6-dihydro-4H-thieno[2,3-c]pyrrol-4-one

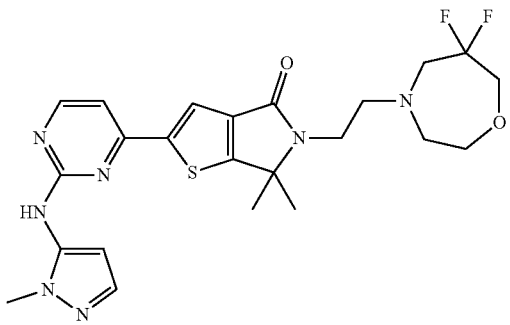 [SMILES: Cn1nccc1Nc1nccc(-c2cc3c(s2)C(C)(C)N(CCN2CCOCC(F)(F)C2)C3=O)n1]

Treat 6,6-difluoro-1,4-oxazepane hydrochloride (200 mg, 0.15 mmol) with carbonate resin (3 molar equivalents) in DCM (5 mL). Rotate the resin suspension for one hour. Remove the solids by filtration and treat the filtrate with p-toluenesulfonic acid (250 mg, 1.45 mmol). Stir the resulting mixture for two hours and then concentrate the mixture under reduced pressure. Add ACN (2 mL) and 2-[6,6-dimethyl-2-{2-[(2-methylpyrazol-3-yl)amino]pyrimidin-4-yl}-4-oxo-thieno[2,3-c]pyrrol-5-yl]ethyl methanesulfonate (200 mg, 0.43 mmol). Treat the resulting solution with triethylamine (0.15 mL, 1.08 mmol). Seal the reaction vessel and heat the mixture at 80° C. for three hours. Cool to room temperature and concentrate the reaction mixture. Purify the residue by reverse phase column chromatography (Column: 50 g C-18; Mobile Phase: A) 0.1% TFA in water, B) 0.1% TFA in ACN; Gradient 10-80% B). Concentrate the fractions containing product. Dissolve the residue in DCM and wash with saturated aqueous sodium bicarbonate solution. Dry the organic solution over anhydrous sodium sulfate, filter and concentrate the filtrate under reduced pressure. Purify the residue by reverse phase column chromatography (Column: 15 g Gold C-18; Mobile Phase: A) 10 mM ammonium carbonate in water with 10% MeOH, B) ACN; Gradient 10-80% B) to give the title compound 16 mg (7%). MS (m/z): 504 (M+1).

EXAMPLE 34

5-{2-[Cyclopropyl(methyl)amino]ethyl}-6,6-dimethyl-2-{2-[(1-methyl-1H-pyrazol-5-yl)amino]pyrimidin-4-yl}-5,6-dihydro-4H-thieno[2,3-c]pyrrol-4-one

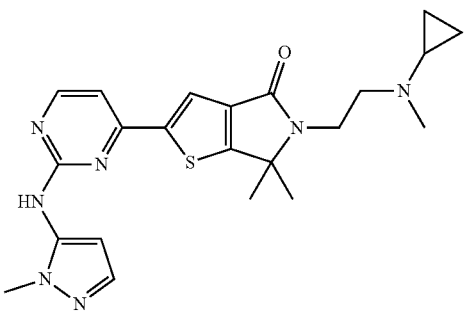 [SMILES: CN(CCN1C(=O)c2cc(-c3ccnc(Nc4ccnn4C)n3)sc2C1(C)C)C1CC1]

Heat a solution of 2-[6,6-dimethyl-2-[2-[(2-methylpyrazol-3-yl)amino]pyrimidin-4-yl]-4-oxo-thieno[2,3-c]pyrrol-5-yl]ethyl methanesulfonate (70 mg, 0.16 mmol) and N-methylcyclopropanamine (77 mg, 1.08 mmol) in DMF (1.7 mL) at 90° C. overnight. Cool the mixture to room temperature. Purify the solution by reverse phase column chromatography (Column: 100 g Gold C-18; Mobile Phase: A) 0.1% formic acid in water, B) 0.1% formic acid ACN; Gradient: 5% B for 5 minutes, gradient to 65% B over 25 minutes; Flow Rate: 60 mL/min) to give the title compound 70 mg (37%). MS (m/z): 438 (M+1).

The following compound is prepared essentially by the method of Example 34.

| Ex. No. | Chemical name | Structure | Physical data MS (m/z): |
|---|---|---|---|
| 35 | 6,6-Dimethyl-2-{2-[(1-methyl-1H-pyrazol-5-yl)amino]pyrimidin-4-yl}-5-[2-(7-oxa-4-azaspiro[2.5]oct-4-yl)ethyl]-5,6-dihydro-4H-thieno[2,3-c]pyrrol-4-one | 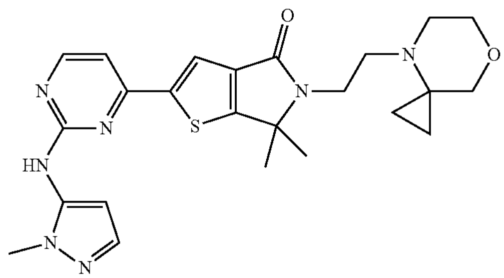 [SMILES: Cn1nccc1Nc1nccc(-c2cc3c(s2)C(C)(C)N(CCN2CCOCC24CC4)C3=O)n1] | 480 (M + 1) |

EXAMPLE 36

2-{2-[(3-Methoxy-1H-pyrazol-4-yl)amino]-5-methylpyrimidin-4-yl}-6,6-dimethyl-5-[2-(morpholin-4-yl)ethyl]-5,6-dihydro-4H-thieno[2,3-c]pyrrol-4-one hydrochloride

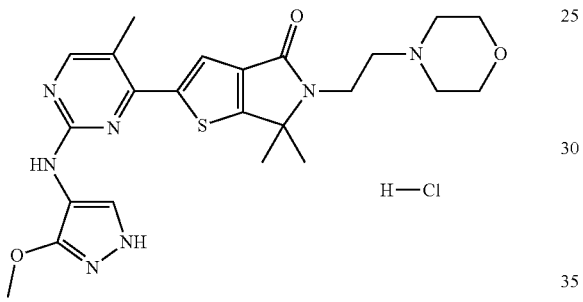

Stir a solution of tert-butyl 4-[[4-[6,6-dimethyl-5-(2-morpholinoethyl)-4-oxo-thieno[2,3-c]pyrrol-2-yl]-5-methyl-pyrimidin-2-yl]amino]-3-methoxy-pyrazole-1-carboxylate (101 mg, 0.173 mmol) and hydrogen chloride (4.0 M in 1,4-dioxane, 2 mL, 8 mmol) in MeOH (20 mL) at room temperature for 12 hours. Concentrate the mixture to dryness to give the title compound 80 mg (89%). MS (m/z): 484 (M+1).

The following compounds are prepared essentially by the method of Example 36.

| Ex. No. | Chemical name | Structure | Physical data MS (m/z): |
|---|---|---|---|
| 37* | 2-{2-[(3-Methoxy-1H-pyrazol-4-yl)amino]pyrimidin-4-yl}-6,6-dimethyl-5-[2-(morpholin-4-yl)ethyl]-5,6-dihydro-4H-thieno[2,3-c]pyrrol-4-one | 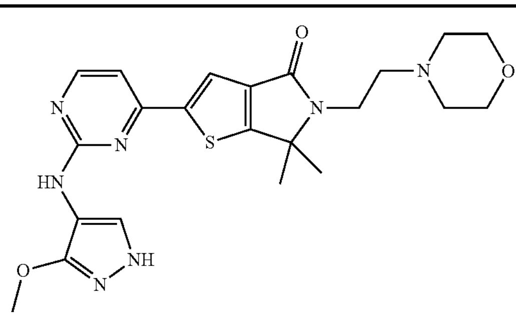 | 470 (M + 1) |

-continued

| Ex. No. | Chemical name | Structure | Physical data MS (m/z): |
|---|---|---|---|
| 38 | 2-{2-[(5-Cyclopropyl-1H-pyrazol-4-yl)amino]pyrimidin-4-yl]-6,6-dimethyl-5-[2-(morpholin-4-yl)ethyl]-5,6-dihydro-4H-thieno[2,3-c]pyrrol-4-one hydrochloride | 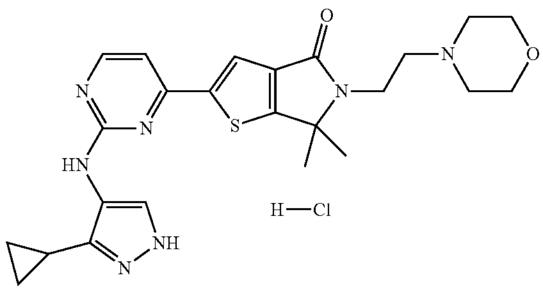 | 480 (M + 1) |
| 39 | 2-{5-Fluoro-2-[(3-methoxy-1H-pyrazol-4-yl)amino]pyrimidin-4-yl}-6,6-dimethyl-5-[2-(morpholin-4-yl)ethyl]-5,6-dihydro-4H-thieno[2,3-c]pyrrol-4-one hydrochloride | 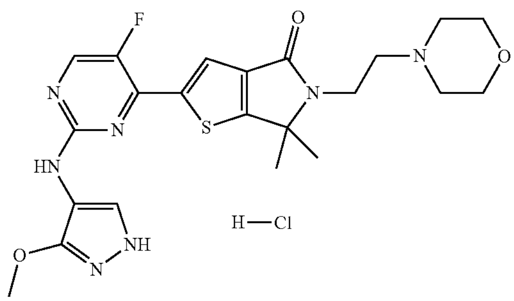 | 488 (M + 1) |

*Free base prepared after reaction

EXAMPLE 40

6,6-Dimethyl-2-{2-[(1-methyl-1H-pyrazol-5-yl)amino]pyrimidin-4-yl}-5-{2-[2-oxa-5-azabicyclo[4.1.0]hept-5-yl]ethyl}-5,6-dihydro-4H-thieno[2,3-c]pyrrol-4-one, isomer 2

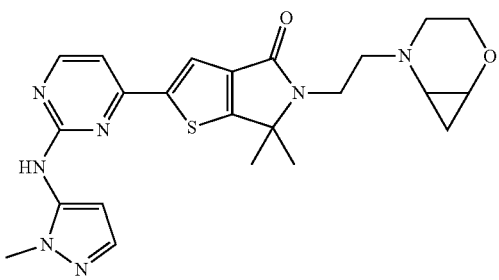 [SMILES: Cn1nccc1Nc1nccc(-c2cc3c(s2)C(C)(C)N(CCN2CCOC4CC42)C3=O)n1]

Purify 6,6-dimethyl-2-{2-[(1-methyl-1H-pyrazol-5-yl)amino]pyrimidin-4-yl}-5-[2-(2-oxa-5-azabicyclo[4.1.0]hept-5-yl)ethyl]-5,6-dihydro-4H-thieno[2,3-c]pyrrol-4-one (Example 30) by chiral column chromatography (Column: Lux Cellulose-4 21.2×250 mm; Mobile Phase: 40% isopropyl alcohol (0.2% isopropylamine)/CO₂); Elution Time: 11 minutes) to give the title compound 24 mg (34%). MS (m/z): 466 (M+1).

X-Ray Powder Diffraction

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2-theta.

X-Ray Powder Diffraction of Example 1, Crystalline Form 1

6,6-Dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one (Crystalline Form 1)

Add 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one (103 mg) to a solution of ACN (1 mL) and water (1 mL) and heat the mixture at 70° C. for 10 minutes. Filter and allow the solution to cool to room temperature overnight. Add water (2 mL) slowly to the solution over the course of five hours. Collect the solids by vacuum filtration and wash with water. Air dry the solids to give the title compound 94 mg (92%).

A prepared sample of Example 1 Crystalline Form 1 is characterized by an XRD pattern using CuKa radiation as having diffraction peaks (2-theta values) as described in Table 1 below, and in particular having peaks at 19.3 degree in combination with one or more of the peaks selected from the group consisting of 15.5, 17.1, 18.0, 20.2, 21.5 and 22.1 degree; with a tolerance for the diffraction angles of 0.2 degrees.

TABLE 1

X-ray powder diffraction peaks of Example 1 Crystalline Form 1

| Peak | Angle (°2-Theta) +/− 0.2 | Relative Intensity (% of most intense peak) |
|---|---|---|
| 1 | 7.1 | 7 |
| 2 | 8.8 | 11 |
| 3 | 12.6 | 7 |
| 4 | 14.3 | 6 |
| 5 | 15.5 | 29 |
| 6 | 16.6 | 15 |
| 7 | 17.1 | 25 |
| 8 | 17.6 | 8 |
| 9 | 18.0 | 63 |
| 10 | 18.7 | 13 |
| 11 | 19.3 | 100 |
| 12 | 20.2 | 24 |
| 13 | 20.7 | 14 |
| 14 | 21.5 | 27 |
| 15 | 22.1 | 26 |
| 16 | 22.8 | 9 |
| 17 | 23.8 | 13 |
| 18 | 24.5 | 10 |
| 19 | 26.4 | 15 |
| 20 | 27.2 | 13 |
| 21 | 28.0 | 9 |
| 22 | 29.3 | 8 |

Several lines of evidence indicate that processes involved in tumor initiation, growth and progression are mediated by activation of one or more signaling pathways in cancer cells. The mitogen-activated protein kinase (MAPK) pathway is a key regulator of cellular proliferation and survival. ERK is a downstream member of this pathway and plays a central role in transmitting extracellular signals from activated receptor tyrosine kinases (RTKs) such as EGFR, FGFR, PDGFR, VEGFR etc. This pathway is a three tiered kinase cascade consisting of the RAF, MEK and ERK (extracellular signal regulated kinase) kinases and the activation of this pathway begins with activation of RAS, a small GTPase. Activation of RAS leads to the recruitment of RAF, a serine/threonine kinase and its activation. Activated RAF then phosphorylates and activates MEK1/2, which in turn phosphorylates and activates ERK1/2. When activated, ERK1/2 phosphorylates several downstream cytoplasmic and nuclear targets involved in cell proliferation, growth, survival and EMT (epithelial-to-mesenchymal transition).

The RAS/MAPK pathway is one of the most important pathways for cell proliferation and it is believed that this pathway is frequently activated in ~30% of all human cancers. Constitutive MAPK pathway activation can result from activating mutations in RAS, BRAF, MEK1, loss of the tumor suppressor NF1 or upstream activation mediated by mutations, amplifications or ligand mediated activation of RTKs. All three RAS family genes (KRAS, NRAS and HRAS) have been shown to be somatically mutated in several cancers including colorectal, melanoma, lung and pancreatic cancer, most commonly as a result of single point mutations at codons 12, 13, and 61. These mutations cause constitutive activation of RAS which is accompanied by increased ERK1/2 activity and growth signaling. Mutations in codons 12, 13 and 61 of KRAS confer resistance to compounds and monoclonal antibodies inhibiting EGFR. KRAS mutations are found in 30% of lung cancers, 90% of pancreatic cancers, 10% of gastric cancers and 50% of colorectal cancers. NRAS mutations were detected in about 10-25% of melanoma. In addition, RAS mutations (HRAS, KRAS, and NRAS) have been identified in ~55-60% of thyroid cancers. Somatic point mutations in BRAF occur in about 8% of human tumors, most frequently in melanoma (60%), colorectal (10%) and thyroid cancers (50%). In melanoma, all BRAF mutations appear to be within kinase domain and a single substitution (T→A, V600E) accounts for 80% of the mutations. BRAF mutations are found, with rare exceptions, in a mutually exclusive pattern with RAS mutations, suggesting that these genetic alterations activate common downstream effectors.

Biological Assays

The following assays demonstrate that the exemplified compounds of the present invention are inhibitors of ERK1 and ERK2 kinase activity. The results of the following assays also demonstrate that the exemplified compounds of the present invention inhibit ERK signaling in cancer cells. Additionally, the compound of Example 1 demonstrates ERK pathway target inhibition in certain xenograft tumor models of cancer. Furthermore, the compound of Example 1 inhibits tumor growth in certain xenograft tumor models of cancer.

ERK1 Kinase Assay

The purpose of this assay is to measure the ability of compounds to inhibit ERK1 kinase activity. Perform the ERK1 kinase assay in vitro using a TR-FRET assay. Start reactions (12.5 µL) by adding 5 µL of ERK1 enzyme (Invitrogen, #PR5254B, final concentration 100 ng/mL) plus substrate GFP-ATF2 (Invitrogen, #PV4445, final concentration 0.2 µM), 5 µL of ATP solution (Invitrogen, #PV3227, final concentration 10 µM) prepared in kinase buffer (50 mM Hepes pH 7.4, 5 mM $MgCl_2$, 0.1 mM EGTA, 0.01% Triton X-100, 1 mM DTT) and 2.5 µL of testing compounds in DMSO solution (final 4%, v/v) in a 384-well PROXI-PLATE™ (Perkin Elmer, #GRN6260). Incubate the reaction mixture at room temperature for 60 minutes. Stop the reaction by addition of 12.5 µL of stop buffer (10 mM EDTA, 2 nM Tb-anti-pATF2 (pThr71) antibody, Invitrogen, #PV4448) in TR-FRET dilution buffer (Invitrogen,

PV3574). Incubate the plates at room temperature for an additional 60 minutes and read on an ENVISION® (PerkinElmer) plate reader at the excitation wavelength 340 nm Calculate the TR-FRET ratio by dividing the GFP acceptor emission signal (at 520 nm) by the Tb donor emission signal (at 495 nm). Calculate percent inhibition using compound treated wells relative to on-plate Max (DMSO control) and Min (No enzyme added) control wells TR-FRET ratio data {% inhibition=100−[(test compound−median Min)/(median Max−median Min)×100]}. Test all compounds at 10 concentrations (20 µM to 0.001 µM) using a 1:3 dilution scheme. Derive Abs_$IC_{50}$ values by fitting percent inhibition and ten-point concentration data to a 4-parameter nonlinear logistic equation (equation 205) using ACTIVITYBASE® 7.3 (ID Business Solutions Limited).

The exemplified compounds within the scope of the invention are tested in this assay substantially as described above. The results of this assay demonstrate that all of the exemplified compounds inhibit ERK1 kinase activity, with $IC_{50}$ values less than 0.15 µM. For example, the compound of Example 1 has an $IC_{50}$ value of 4.86 nM (±0.20, n=7).

ERK2 Kinase Assay

The purpose of this assay is to measure the ability of compounds to inhibit ERK2 kinase activity. Perform the ERK2 kinase assay in vitro using a TR-FRET assay. Start all reactions (12.5 µL) by adding 5 µL of ERK2 enzyme (Invitrogen, #PV3595B, final conc 50 ng/mL) plus substrate GFP-ATF2 (Invitrogen, #PV4445, final conc 0.2 µM), 5 µL of ATP solution (Invitrogen, #PV3227, final conc 10 µM) prepared in kinase buffer (50 mM Hepes pH 7.4, 5 mM $MgCl_2$, 0.1 mM EGTA, 0.01% Triton X-100, 1 mM DTT) and 2.5 µL of testing compounds in DMSO solution (final 4%, v/v) in a 384-well PROXIPLATE™ (Perkin Elmer, #GRN6260). Incubate reactions at room temperature for 60 minutes. Stop reactions by addition of 12.5 µL of stop buffer (10 mM EDTA, 2 nM Tb-anti-pATF2 (pThr71) antibody, Invitrogen, #PV4448) in TR-FRET dilution buffer (Invitrogen, #PV3574). Incubate the plates at room temperature for an additional 60 minutes and read ON ENVISION® (PerkinElmer) plate reader at the excitation wavelength of 340 nm Calculate a TR-FRET ratio by dividing the GFP acceptor emission signal (at 520 nm) by the Tb donor emission signal (at 495 nm). Calculate percent inhibition using compound wells relative to on-plate Max (DMSO control) and Min (No enzyme added) control wells TR-FRET ratio data {% inhibition=100−[(test compound−median Min)/(median Max−median Min)×100]}. Test all compounds at 10 concentrations (20 µM to 0.001 µM) using a 1:3 dilution scheme. Derive Abs_IC50 values by fitting percent inhibition and ten-point concentration data to a 4-parameter nonlinear logistic equation (equation 205) using ACTIVITYBASE 7.3 (ID Business Solutions Limited).

The exemplified compounds within the scope of the invention are tested in this assay substantially as described above. The results of this assay demonstrate that all of the exemplified compounds inhibit ERK2 kinase activity, with $IC_{50}$ values less than 0.15 µM. For example, the compound of Example 1 has an $IC_{50}$ value of 5.24 nM (±0.24, n=7).

ERK1/2 Cell Mechanistic Assay (pRSK1 Alphascreen Assay)

The purpose of this assay is to measure the ability of compounds to inhibit ERK signaling in cancer cells in vitro. Carry out the pRSK1 Alphascreen assay using the HCT116 colorectal cancer cell line (ATCC, #CCL-247). Routinely culture HCT116 cells in Dulbecco's Modified Eagle's Medium (DMEM) (Hyclone, #SH30022) growth medium containing 5% Fetal Bovine Serum (FBS) (Gibco, #16000-044) in T-150 flasks and incubate in a 5% $CO_2$ incubator at 37° C. Harvest cells when they become confluent and freeze in freezing medium at $1×10e^7$ cells/mL as "assay ready frozen cells" and store in liquid nitrogen. To run the assay, plate 40,000 HCT116 cells/well in a 96-well tissue culture plate and incubate at 37° C. in a 5% $CO_2$ incubator overnight. Test compounds at 10 concentrations starting at a 20 µM top concentration and utilize a 1:3 dilution scheme (20 µM to 0.001 µM) with a final DMSO concentration of 0.5% (v/v). Add compounds in 20 µL serum free growth medium and incubate at 37° C. for two hours. Remove growth medium and add 50 µL of 1× lysis buffer [Cell Signaling Technology, #9803] containing 1× holt protease and phosphate inhibitor cocktail [Thermo, #78441] to each well and incubate at room temperature for 10 minutes on a shaker. Transfer 4 µL of cell lysate from each well to respective wells in a 384 well assay plate [Perkin Elmer, #6006280] and add 5 µL of reaction mix [2000 parts 1× assay buffer (Perkin Elmer, #A1000), 1 part biotin-RSK1 antibody (Santa Cruz, #sc-231-B-G), 4 parts pRSK1 antibody (Abcam, #ab32413), 35 parts acceptor beads (Perkin Elmer, #6760617R)]. Seal the plate with foil plate seal (Beckman Coulter, #538619) and incubate at room temperature for two hours. Add 2 µL of donor beads [20 parts 1× assay buffer, 1 part donor beads] to each well and seal the plate with clear plate seal (Applied Biosystems, #4311971) and incubate at room temperature in the dark for two hours. Measure the fluorescence intensity in each well by reading the plates in ENVISION® (PerkinElmer) plate reader. Derive the Rel $IC_{50}$ values by fitting percent pRSK1 inhibition [% inhibition=100−[(test compound−median Min)/(median Max−median Min)×100] and ten-point concentration data to a 4-parameter nonlinear logistic equation (Abase equation 205) using ACTIVITYBASE® 7.3 (ID Business Solutions Limited).

The exemplified compounds within the scope of the invention are tested in this assay substantially as described above. The results of this assay demonstrate that all of the exemplified compounds inhibit ERK substrate (RSK) phosphorylation in tumor cells, with $IC_{50}$ values less than 3 µM. For example, the compound of Example 1 has an $IC_{50}$ value of 0.429 µM (±0.173, n=8).

In Vivo Target Inhibition (IVTI) Assay (pRSK1 ELISA Assay)

The purpose of this assay is to measure the ability of a test compound to inhibit ERK1/2 substrate phosphorylation in an animal model Implant female athymic nude mice (22-25 g) from Harlan Laboratories with $5×10e^6$ HCT116 colorectal cancer cells (ATCC, #CCL-247) subcutaneously in the right flank region in 200 µL of 1:1 Hank's Balanced Salt Solution (HBSS)+Matrigel solution. Measure tumor growth and body weight twice per week beginning the seventh day after the implantation. When tumor sizes reach 300-500 $mm^3$, randomize animals and group into groups of five animals. Dose animals with either compound at an appropriate dose in a compound specific vehicle or vehicle alone (vehicle: 1% HEC/0.25% Tween 80/0.05% Antifoam) orally and collect tumors and blood at desired time intervals after dosing. Sacrifice animals using isoflurane anesthesia plus cervical dislocation. Flash freeze tumors and store at −80° C. until processing for pRSK1 levels by ELISA assay. Collect blood in EDTA tubes and spin down for plasma and freeze at −80° C. in a 96-well plate. Determine compound exposures using standard methods.

Pulverize tumors in liquid nitrogen and lyse in 1× lysis buffer (MSD, #R60TX-3) containing 1× halt protease & phosphatase inhibitor cocktail (Thermo Scientific, #0861281), 1 mM phenylmethanesulfonyl fluoride (PMSF) (Sigma, #93482-50ML-F) and 1 μM sodium metavanadate (Sigma, #590088) using Matrix D beads (MP Biomedical, #6913-500) in a FastPrep-24™ Cell Disrupter machine (MP Biomedical) in a cold room (4° C.). Transfer tumor lysates to fresh tubes after spinning at 14000 rpm for 20 minutes at 4° C. Determine protein concentration of tumor or cell lysates using Pierce BCA Protein Assay Kit (cat#23225, Thermo Scientific). This kit contains three main components—(1) BCA Reagent A, containing sodium carbonate, sodium bicarbonate, bicinchoninic acid and sodium tartarate in 0.1 M sodium hydroxide, (2) BCA Reagent B, containing 4% cupric sulfate, and (3) Albumin standard ampules, containing 2 mg/mL in 0.9% saline and 0.05% sodium azide. In a 96-well plate, add bovine serum albumin protein standard for a concentration range of 20-2000 ug/mL in 25 μL in duplicate wells to generate a standard curve. Add cell or tumor lysates diluted in 25 μL 1×PBS to duplicate test wells. Prepare working BCA reagent by adding 2% Reagent B to Reagent A (2 mL of B+98 mL of A), mix well and add 200 μL to each sample or standard. Mix well, cover the plate and incubate at 37° C. for 30 minutes. Cool plate to room temperature and measure the absorbance at or near 562 nm on a plate reader (Envision plate reader from Perkin Elmer). Subtract the average 562 nm absorbance measurement of the blank standard replicates from the 562 nm measurements of all other individual standard and unknown (cell or tumor lysate) sample replicates. Prepare a standard curve by plotting the average blank-corrected 562 nm measurement for each bovine serum albumin standard versus its concentration in μg/mL. Use the standard curve to determine the protein concentration of each unknown samples using curve-fit logarithms in Microsoft Excel. Freeze remaining tumor lysates at −80° C. Use once freeze-thawed tumor lysates to measure pRSK1 expression by sandwich ELISA.

Coat 96-well plates (Thermo, #15042) overnight at 4° C. with 40 ng of RSK1 goat antibody (Santa Cruz, #sc-231-G) and incubate at room temperature for one hour and then at 4° C. overnight. Wash plates three times with 300 μL of PBST (1× phosphate buffered saline (PBS) containing 0.05% Tween-20), block with 100 μL per well of blocking buffer (Thermo Scientific, #37532) and incubated at room temperature for two hours. Wash plates three times with 300 μL PBST and transfer 20 μg of tumor lysate to each well and incubate at 4° C. overnight. Wash plates three times with 300 μL PB ST and incubate with 100 μL of pRSK1 (T359/5363) rabbit antibody (1:1000 dilution in blocking buffer) at room temperature for four hours. Wash plates three times with 300 μL PBST and incubate with 100 μL anti-rabbit HRP-conjugated secondary antibody (GE Healthcare UK, #NA934V; diluted 1:10000 in blocking buffer) Incubate at room temperature for one hour. Wash plates three times with 300 μL of PBST, add 100 μL of SUPERSIGNAL® ELISA Femto maximum sensitivity substrate (Thermo, #37075) and incubate on a shaker for one minute. Determine the luminescence signal using an ENVISION® plate reader. Determine the pRSK1 level in each tumor lysate by considering tumor lysates from animals treated with vehicle alone as 100%. Analyze each sample in duplicate and use average numbers for calculations. Calculate TED$_{50}$ using Excel and XL Fit.

A compound within the scope of the invention is tested in this assay substantially as described above. The results of this assay demonstrates that the compound of Example 1 inhibits RSK1 phosphorylation in a tumor xenograft model. For example, the compound of Example 1 has a TED$_{50}$ value of 16 mg/kg.

Xenograft Tumor Models

The purpose of this assay is to measure reduction in tumor volume in response to test compound administration. Expand human colorectal cancer cells HCT116 (ATCC, # CCL-247) in culture, harvest and inject 5×10e$^6$ cells in 200 μL of 1:1 HBSS+matrigel solution subcutaneously on to the rear right flank of female athymic nude mice (22-25 g, Harlan Laboratories). Expand human pancreatic cancer cells MIA PACA-2 (ATCC, # CRL-1420) or human non-small cell lung cancer cells CALU-6 (ATCC, #HTB-56) or human colorectal cancer cells COLO-205 (ATCC, #CCL-222) in culture, harvest and inject 5×10e$^6$ cells in 200 μL of 1:1 HBSS+matrigel solution subcutaneously on to the rear right flank of female athymic nude mice (22-25 g, Harlan Laboratories). Measure tumor growth and body weight twice per week beginning the seventh day after the implantation. When tumor sizes reach 200-400 mm$^3$, randomize animals and group into groups of eight to ten animals. Prepare test compound in an appropriate vehicle (vehicle: 1% HEC/ 0.25% Tween 80/0.05% Antifoam) and administer by oral gavage for 14 to 21 days. Tumor response is determined by tumor volume measurement performed twice a week during the course of treatment. Body weight is taken as a general measure of toxicity.

A compound within the scope of invention is tested in this assay run substantially as above. The compound of Example 1 is found to have delta T/C % values as provided in Table 2 below. These results indicate that the compound of Example 1 demonstrates significant anti-tumor activity in several human cancer xenograft models including HCT116, MIA PACA-2, CALU-6 and COLO-205.

TABLE 2

Efficacy of Example 1 in xenograft models

| Tumor Model | Dose (mg/kg) | Schedule | p-value | Delta T/C % or Regr % | TGI % |
|---|---|---|---|---|---|
| HCT116 | 25 | QD | | −8 | 108 |
| HCT116 | 50 | QD | <0.001* | 11 | 89 |
| HCT116 | 100 | QD | <0.001* | −25 | 125 |
| MIA PACA-2 | 12.5 | QD | 0.003* | 32 | 68 |
| MIA PACA-2 | 25 | QD | <0.001* | 2 | 98 |
| MIA PACA-2 | 50 | QD | <0.001* | −22 | 122 |
| MIA PACA-2 | 100 | QD | <0.001* | −66 | 166 |
| CALU-6 | 12.5 | QD | 0.010* | 22 | 78 |
| CALU-6 | 25 | QD | 0.005* | 14 | 86 |
| CALU-6 | 50 | QD | <0.001* | −31 | 131 |
| CALU-6 | 100 | QD | <0.001* | −77 | 177 |
| COLO-205 | 12.5 | QD | <0.001* | −19 | 119 |

TABLE 2-continued

Efficacy of Example 1 in xenograft models

| Tumor Model | Dose (mg/kg) | Schedule | p-value | Delta T/C % or Regr % | TGI % |
|---|---|---|---|---|---|
| COLO-205 | 25 | QD | <0.001* | −32 | 132 |
| COLO-205 | 100 | QD | <0.001* | −76 | 176 |

Analysis for tumor volume is based on Log 10 and SpatialPower covariance structure.
*: significant (p < 0.05)
NA: Not applicable
Delta T/C % is calculated when the endpoint tumor volume in a treated group is at or above baseline tumor volume. The formula is $100 * (T - T_0)/(C - C_0)$, where T and C are mean endpoint tumor volumes in the treated or control group, respectively. $T_0$ and $C_0$ are mean baseline tumor volumes in those groups.
Regression % is calculated when the endpoint volume is below baseline. The formula is $100 * (T - T_0)/T_0$ Where $T_0$ is the mean baseline tumor volume for the treated group. For HCT116, MIA PACA-2 and CALU-6, models, grand mean of all groups from baseline (randomization) at day 10, day 20 and day 15, respectively was used to compute % change of T/C.

In Vivo Combination Studies

Due to tumor heterogeneity combination therapy has become essential in certain types of cancer treatment for effective therapy or to overcome acquired resistance. It is hypothesized that a combination of targeted therapies has the potential to be more effective in slowing or even halting cancers. In that context, the compound of Example 1 is tested for tumor growth inhibition in combination with a pan-RAF inhibitor compound (see WO 2013/134243, 1-(3,3-dimethylbutyl)-3-(2-fluoro-4-methyl-5-(7-methyl-2-(methylamino)pyrido[2,3-d]pyrimidin-6-yl)phenyl)urea, hereinafter "the pan-RAF inhibitor compound"), a CDK4/6 inhibitor compound (see WO 2010/075074, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof), hereinafter "the CDK4/6 inhibitor compound"), or DC101 (see, for example, Witte L., et al Cancer Metastasis Rev., 17,155-161, 1998, rat monoclonal antibody directed against mouse VEGFR2 that may be used in experiments as a surrogate in mice for an anti-VEGFR2 Ab, preferably ramucirumab (see WO 2003/075840, also known as Cyramza®, IMC-1121b, CAS registry number 947687-13-0)). More specifically, the compound of Example 1 is tested in combination with either the pan-RAF inhibitor compound or the CDK4/6 inhibitor compound in HCT116, a KRAS mutant colorectal cancer xenograft model. Also, the compound of Example 1 is tested in combination with either the CDK4/6 inhibitor compound or DC101 in NCI-H441, A549, and NCI-H2122, KRAS mutant non-small cell lung cancer (NSCLC) xenograft models.

The HCT116 combination efficacy study is done in athymic nude rats. Expand human colorectal cancer cells HCT116 (ATCC, #CCL-247) in culture, harvest and inject $5 \times 10e^6$ cells in 200 μL of 1:1 HBSS+matrigel solution subcutaneously on to the rear right flank of female NIH nude rats (120-145 gm, Taconic Farms). Measure tumor growth and body weight twice per week beginning the seventh day after the implantation. When average tumor sizes reach 200-300 mm$^3$, randomize animals and group into groups of five to seven animals. Prepare test compound in an appropriate vehicle (see below) and administer by oral gavage for 21 to 28 days. Tumor response is determined by tumor volume measurement performed twice a week during the course of treatment. Vehicle used in this study is 1% HEC (hydroxy ethyl cellulose)/0.25% Tween® 80/0.05% Antifoam. The compound of Example 1 and the pan-RAF inhibitor compound are formulated in 1% HEC/0.25% Tween® 80/0.05% Antifoam. The CDK4/6 inhibitor compound is formulated in 1% HEC in 25 mM Sodium phosphate buffer, pH 2. Administration of the compound of Example 1 at 10 mpk and 20 mpk QD results in single agent activity of 52% and 64% tumor growth inhibition respectively (Table 3). In contrast, administration of the pan-RAF inhibitor compound at 10 mpk and 20 mpk BID results in single agent activity of 29% and 68%, respectively. All treatments are statistically significant (p<0.05) from vehicle control except the pan-RAF inhibitor compound at 10 mpk BID. Administration of the compound of Example 1 at 10 mpk, QD in combination with the pan-RAF inhibitor compound at 10 mpk, BID results in 94% tumor growth inhibition (p<0.001) and the combination result is "Synergistic" as calculated by Bliss Independence method (Table 3). This combination appears to be tolerated as there is no significant body weight loss. Administration of the compound of Example 1 at 10 mpk, QD in combination with the pan-RAF inhibitor compound at 20 mpk, BID has also results in significant (p<0.05) tumor growth inhibition (95%) and the combination result is "Additive" "as calculated by Bliss Independence method (Table 3). This combination appears to be tolerated as there is no significant body weight loss. In the same study, administration of the compound of Example 1 at 10 mpk, QD with the CDK4/6 inhibitor compound at 20 mpk QD results in 98% tumor growth inhibition whereas single agent efficacy of the compound of Example 1 and the CDK4/6 inhibitor compound are 52% and 76% tumor growth inhibition, respectively. Combination of these two agents show a statistically significant "Additive" result as calculated by Bliss Independence method (Table 3). This combination appears to be tolerated as there is no significant body weight loss. These results suggest that combination of the compound of Example 1 with either the pan-RAFinhibitor compound or the CDK4/6 inhibitor compound may provide greater benefit to patients having KRAS mutant colorectal cancer.

TABLE 3

Combination studies of the compound of Example 1 with the pan-RAF inhibitor compound, or the CDK4/6 inhibitor compound in HCT116 KRAS mutant colorectal cancer xenograft model

| Treatment | Compound | Dose (mg/kg) | Schedule | Delta T/C % | TGI % | p-value | Combination Result** |
|---|---|---|---|---|---|---|---|
| 1 | Vehicle | NA | BID | NA | NA | NA | NA |
| 2 | Example 1 | 10 | QD | 48 | 52 | 0.038* | NA |
| 3 | Example 1 | 20 | QD | 36 | 64 | 0.005* | NA |
| 4 | pan-RAF inhibitor | 10 | BID | 71 | 29 | 0.303 | NA |
| 5 | pan-RAF inhibitor | 20 | BID | 32 | 68 | 0.001* | NA |

TABLE 3-continued

Combination studies of the compound of Example 1 with the pan-RAF inhibitor compound, or the CDK4/6 inhibitor compound in HCT116 KRAS mutant colorectal cancer xenograft model

| Treatment | Compound | Dose (mg/kg) | Schedule | Delta T/C % | TGI % | p-value | Combination Result** |
|---|---|---|---|---|---|---|---|
| 6 | CDK4/6 inhibitor | 20 | QD | 24 | 76 | <0.001* | NA |
| 7 | Example 1 + pan-RAF inhibitor | 10, 10 | QD, BID | 6 | 94 | <0.001* | Synergistc |
| 8 | Example 1 + pan-RAF inhibitor | 10, 20 | QD, BID | 5 | 95 | <0.001* | Additive |
| 9 | Example 1 + CDK4/6 inhibitor | 10, 20 | QD, QD | 2 | 98 | <0.001* | Additive |

Analysis for tumor volume is based on Log 10 and SpatialPower covariance structure.
*significant ($p < 0.05$)
**The statistical effect of the combination of two agents is determined by Bliss Independence method: First, a repeated measures model is fit to log tumor volume vs. group, time and group-by-time. Then contrast statements are used to test for an interaction effect at each time point. The expected additive response (EAR) for the combination is calculated on the tumor volume scale as, EAR volume = V1 * V2/V0, where V0, V1, and V2 are the estimated mean tumor volumes for the vehicle control, treatment 1 alone, and treatment 2 alone, respectively. If the interaction test is significant ($p < 0.05$), the combination effect is declared synergistic if the observed combination volume is less than the EAR volume, antagonistic if the observed combination volume is greater than the EAR volume, or additive otherwise, at the doses and schedules that are tested.
NA: Not applicable
Delta T/C % is calculated when the endpoint tumor volume in a treated group is at or above baseline tumor volume. The formula is $100 * (T - T_0)/(C - C_0)$, where T and C are mean endpoint tumor volumes in the treated or control group, respectively. $T_0$ and $C_0$ are mean baseline tumor volumes in those groups.
Dose for 28 days in all studies
Grand mean of all groups from baseline (randomization) at day 11 was used to compute % change of T/C Combination efficacy is also tested in three KRAS mutant NSCLC xenograft models including A549 (KRAS_G12S) in SCID mice as well as NCI-H441 (KRAS_G12V) and NCI-H2122 (KRAS_G12C) in athymic nude mice. Expand human non-small cell lung cancer cells NCI-H441 (ATCC, #CRL-5807) and NCI-H2122 (ATCC, #CRL-5985) in culture, harvest and inject $5\times10e^6$ cells in 200 μL of 1:1 HBSS+matrigel solution subcutaneously on to the rear right flank of female athymic nude mice (20-22 gm, Harlan Laboratories). Expand human non-small cell lung cancer cells A549 (ATCC, #CC1-185) in culture, harvest and inject $5\times10e^6$ cells in 200 μL of 1:1 HBSS+matrigel solution subcutaneously on to the rear right flank of female CB-17 SCID mice (18-20 gm, Taconic Farms). For all cell lines, measure tumor growth and body weight twice per week beginning the seventh day after the implantation. When average tumor sizes reach 200-300 mm³, randomize animals and group into groups of five to seven animals. Prepare test compound in an appropriate vehicle (see below) and administer by oral gavage (compound of Example 1 and the CDK4/6 inhibitor compound) or intraperitoneally (DC101) for 21 to 28 days. Tumor response is determined by tumor volume measurement performed twice a week during the course of treatment. Vehicle used in these studies is 1% HEC/0.25% Tween® 80/0.05% Antifoam. The compound of Example 1 is formulated in 1% HEC/0.25% Tween® 80/0.05% Antifoam and the CDK4/6 inhibitor compound is formulated in 1% HEC in 25 mM sodium phosphate buffer, pH 2. The administration of the compound of Example 1 as a single agent at 50 mpk results in 41% and 91% tumor growth inhibition in NCI-H2122 and A549 tumors respectively; and leads to 101% tumor growth inhibition (i.e., 1% tumor regression) in NCI-H441 tumors. Administration of the CDK4/6 inhibitor compound as single agent at 50 mpk results in 53%, 51% and 81% tumor growth inhibition in NCI-H2122, A549 and NCI-H441 models respectively. Also, the combination of the compound of Example 1 (50 mpk) with the CDK4/6 inhibitor compound (50 mpk) results in 151% (i.e. 51% regression) and 147% (i.e. 47% regression) tumor growth inhibition in A549 and NCI-H441 tumors respectively; and 82% tumor growth inhibition in NCI-H2122 tumors. The combination result in all three tumor models are "Additive" as calculated by Bliss Independence method (Table 4). In general, all treatments appear to be tolerated in these studies as indicated by no significant body weight loss. In the same NCI-H441 xenograft model, DC101 in phosphate buffer is also administered intraperitoneally twice per week (BIW) as a single agent or in combination with the compound of Example 1, 50 mpk, QD for 28 days. Administration of DC101 at 20 mpk BIW results in a single agent activity of 102% tumor growth inhibition (i.e. 2% regression). Combination of the compound of Example 1 at 50 mpk, QD with DC101 at 20 mpk, BIW results in 146% tumor growth inhibition (i.e. 46% regression). This combination result is "Additive" as calculated by Bliss Independence method (Table 4). This combination appears to be tolerated as there is no significant body weight loss. These results suggest that combination of the compound of Example 1 with either the CDK4/6 inhibitor compound or an anti-VEGFR2 antibody may provide greater benefit to non-small cell lung cancer patients with KRAS mutation.

TABLE 4

Combination studies of the compound of Example 1 with the CDK4/6 inhibitor compound or DC101 in KRAS mutant non-small cell lung cancer xenograft models

| Tumor Model | Treatment | Compound | Dose (mg/kg) | Schedule[+] | Delta T/C % | Regression % | p-value (vs. Vehicle) | Combination Effect[**] |
|---|---|---|---|---|---|---|---|---|
| NCI-H441 NSCLC Model | 1 | Vehicle | NA | QD | NA | NA | NA | NA |
| | 2 | CDK4/6 inhibitor | 50 | QD | 19 | NA | <0.001* | NA |
| | 3 | DC101 | 20 | BIW | NA | 2 | <0.001* | NA |
| | 4 | Example 1 | 50 | QD | NA | 1 | <0.001* | NA |
| | 5 | Example 1 + DC101 | 50 20 | QD BIW | NA | 46 | <0.001* | Additive |
| | 6 | Example 1 + CDK4/6 inhibitor | 50 50 | QD QD | NA | 47 | <0.001* | Additive |
| A549 NSCLC Model | 1 | Vehicle | NA | QD | NA | NA | NA | NA |
| | 2 | CDK4/6 inhibitor | 50 | QD | 49 | NA | 0.033* | NA |
| | 3 | Example 1 | 50 | QD | 9 | NA | <0.001* | NA |
| | 4 | Example 1 + CDK4/6 inhibitor | 50 50 | QD QD | NA | 51 | <0.001* | Additive |
| NCI-H2122 NSCLC Model | 1 | Vehicle | NA | QD | NA | NA | NA | NA |
| | 2 | CDK4/6 inhibitor | 50 | QD | 47 | NA | 0.008* | NA |
| | 3 | Example 1 | 50 | QD | 59 | NA | 0.055 | NA |
| | 4 | Example 1 + CDK4/6 inhibitor | 50 50 | QD QD | 18 | NA | <0.001* | Additive |

[+]Analysis for tumor volume is based on Log 10 transformation and a repeated measures ANOVA with a special power covariance structure
*significant ($p < 0.05$)
[**]The statistical effect of the combination of two agents is determined by Bliss Independence method: First, a repeated measures model is fit to log tumor volume vs. group, time and group-by-time. Then contrast statements are used to test for an interaction effect at each time point. The expected additive response (EAR) for the combination is calculated on the tumor volume scale as, EAR volume = V1 * V2/V0, where V0, V1, and V2 are the estimated mean tumor volumes for the vehicle control, treatment 1 alone, and treatment alone, respectively. If the interaction test is significant ($p < 0.05$), the combination effect is declared synergistic if the observed combination volume is less than the EAR volume, antagonistic if the observed combination volume is greater than the EAR volume, or additive otherwise, at the doses and schedules that are tested.
NA: Not applicable
Delta T/C % is calculated when the endpoint tumor volume in a treated group is at or above baseline tumor volume. The formula is $100 * (T - T_0)/(C - C_0)$, where $T_0$ and $C_0$ are mean endpoint tumor volumes in the treated or control group, respectively. $T_0$ and $C_0$ are mean baseline tumor volumes in those groups. Baseline (randomization) at day 11 (HCT116), day 25 (NCI-H441), day 22 (A549), day 18 (NCI-H2122) are used to compute % change of T/C.
Dose for 28 days in all studies.

We claim:

1. A compound of the formula:

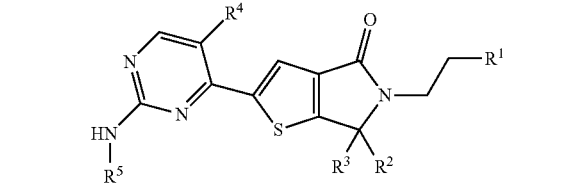

wherein:

$R^1$ is

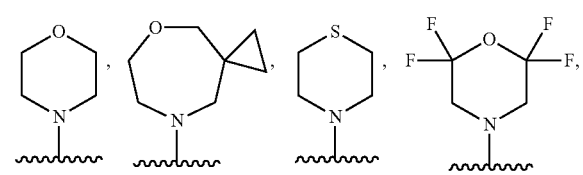

-continued $R^2$ and $R^3$ are methyl or $R^2$ and $R^3$ can be taken together to form cyclopropyl;

$R^4$ is hydrogen, methyl, chloro, fluoro, or trifluoromethyl; and

R⁵ is

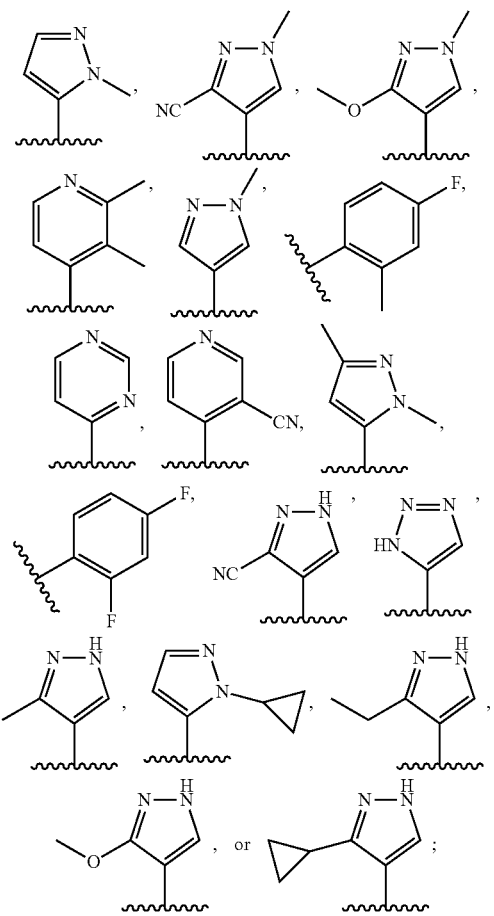

or a pharmaceutically acceptable salt thereof.

2. The compound or salt according to claim 1 wherein R² and R³ are independently methyl.

3. The compound or salt according to claim 2 wherein R⁴ is hydrogen.

4. The compound or salt according to claim 3 wherein R¹ is

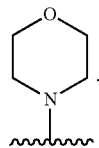

5. The compound or salt according to claim 3 wherein R⁵ is

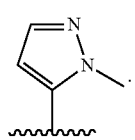 [SMILES: *c1ccnn1C]

6. The compound or salt according to claim 4 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

7. The compound according to claim 6 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

8. A pharmaceutical composition comprising a compound of the formula:

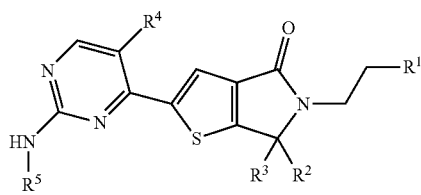

wherein:

R¹ is

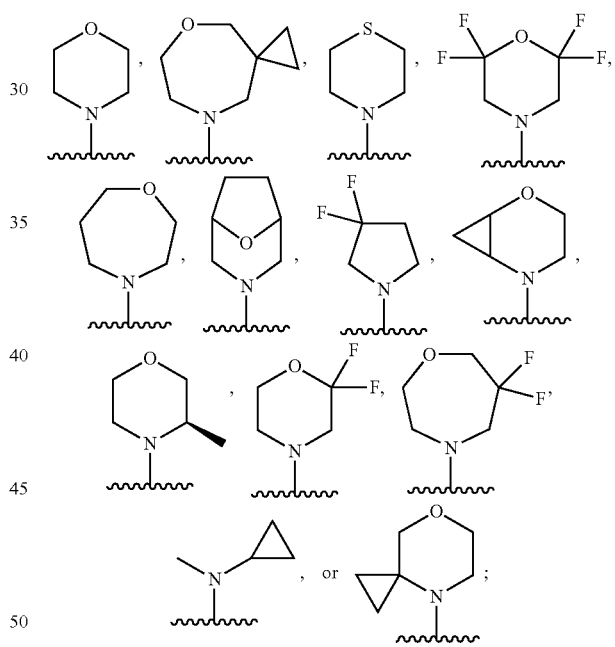

R² and R³ are methyl or R² and R³ can be taken together to form cyclopropyl;

R⁴ is hydrogen, methyl, chloro, fluoro, or trifluoromethyl; and

R⁵ is

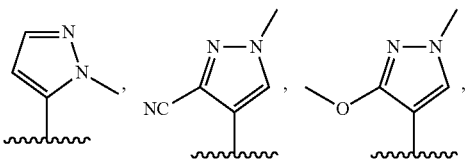

-continued

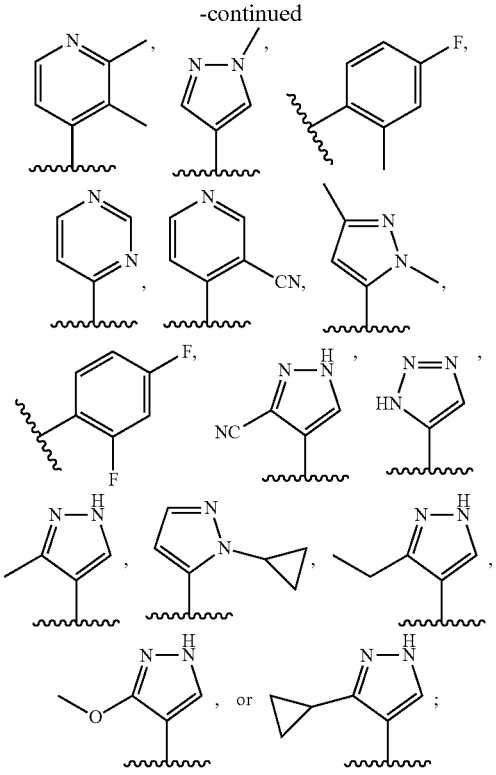

or a pharmaceutically acceptable salt thereof, and a pharmaceutically acceptable carrier, diluent, or excipient.

9. The pharmaceutical composition according to claim 8 wherein $R^2$ and $R^3$ are independently methyl.

10. The pharmaceutical composition according to claim 9 wherein $R^4$ is hydrogen.

11. The pharmaceutical composition according to claim 10 wherein $R^1$ is

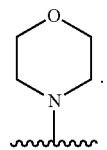

12. The pharmaceutical composition according to claim 10 wherein $R^5$ is

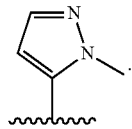

13. The pharmaceutical composition according to claim 11 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

14. The pharmaceutical composition according to claim 13 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

15. A method of treating cancer, comprising administering to a patient in need thereof, an effective amount of a compound of the formula:

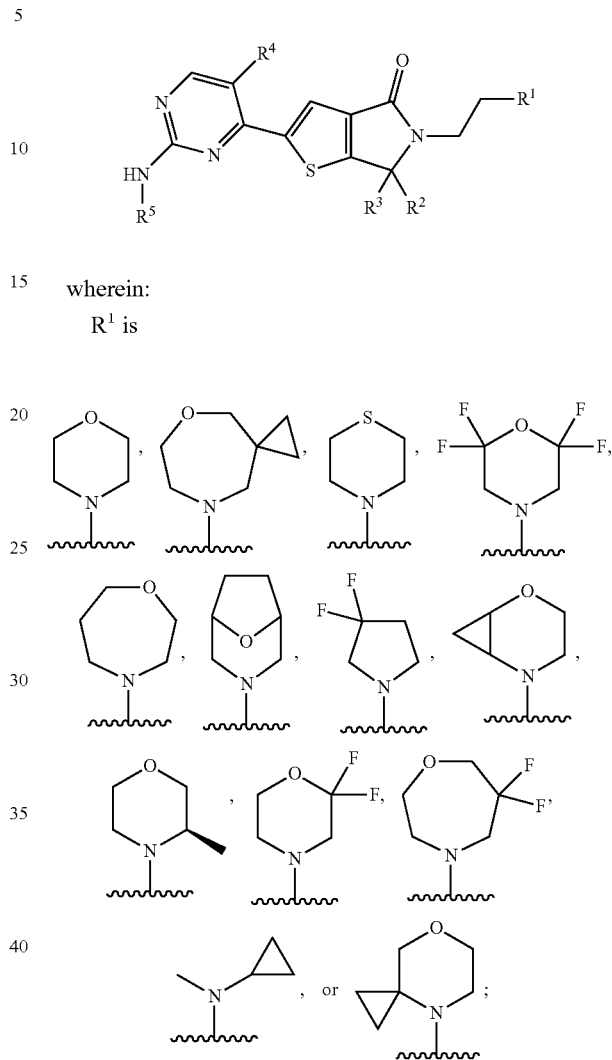

wherein:

$R^1$ is $R^2$ and $R^3$ are methyl or $R^2$ and $R^3$ can be taken together to form cyclopropyl;

$R^4$ is hydrogen, methyl, chloro, fluoro, or trifluoromethyl; and $R^5$ is

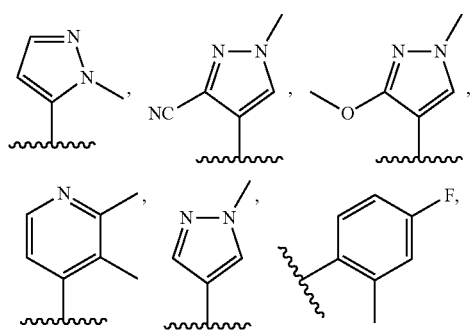

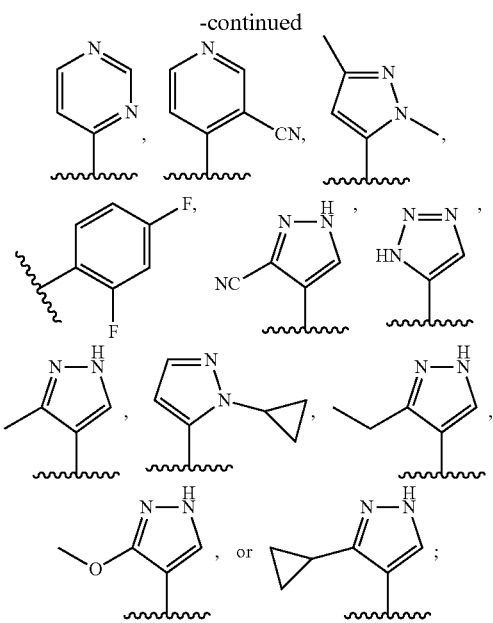

or a pharmaceutically acceptable salt thereof, wherein the cancer is selected from the group consisting of melanoma, colorectal cancer, pancreatic cancer, and non-small cell lung cancer.

16. The method according to claim 15 wherein $R^2$ and $R^3$ are independently methyl.

17. The method according to claim 16 wherein $R^4$ is hydrogen.

18. The method according to claim 17 wherein $R^1$ is

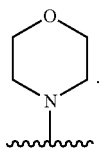

19. The compound or salt according to claim 17 wherein $R^5$ is

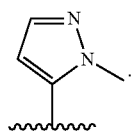

20. The compound or salt according to claim 18 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

21. The compound according to claim 20 which is 6,6-dimethyl-2-{2-[(1-methyl-1H-pyrazol-5-yl)amino]pyrimidin-4-yl}-5-[2-(morpholin-4-yl)ethyl]-5,6-dihydro-4H-thieno[2,3-c]pyrrol-4-one.

22. The method according to claim 15, wherein the cancer is colorectal cancer.

23. The method according to claim 16, wherein the cancer is colorectal cancer.

24. The method according to claim 17, wherein the cancer is colorectal cancer.

25. The method according to claim 18, wherein the cancer is colorectal cancer.

26. The method according to claim 19, wherein the cancer is colorectal cancer.

27. The method according to claim 20, wherein the cancer is colorectal cancer.

28. The method according to claim 21, wherein the cancer is colorectal cancer.

29. The method according to claim 15, wherein the cancer is pancreatic cancer.

30. The method according to claim 16, wherein the cancer is pancreatic cancer.

31. The method according to claim 17, wherein the cancer is pancreatic cancer.

32. The method according to claim 18, wherein the cancer is pancreatic cancer.

33. The method according to claim 19, wherein the cancer is pancreatic cancer.

34. The method according to claim 20, wherein the cancer is pancreatic cancer.

35. The method according to claim 21, wherein the cancer is pancreatic cancer.

36. The method according to claim 15, wherein the cancer is non-small cell lung cancer.

37. The method according to claim 16, wherein the cancer is non-small cell lung cancer.

38. The method according to claim 17, wherein the cancer is non-small cell lung cancer.

39. The method according to claim 18, wherein the cancer is non-small cell lung cancer.

40. The method according to claim 19, wherein the cancer is non-small cell lung cancer.

41. The method according to claim 20, wherein the cancer is non-small cell lung cancer.

42. The method according to claim 21, wherein the cancer is non-small cell lung cancer.

* * * * *